United States Patent
Cottone et al.

(10) Patent No.: US 9,572,693 B2
(45) Date of Patent: Feb. 21, 2017

(54) SELF-EXPANDING STENT WITH POLYGON TRANSITION ZONE

(75) Inventors: Robert J. Cottone, Davie, FL (US); Shusheng Ye, Davie, FL (US)

(73) Assignee: Orbusneich Medical, Inc., Fort Lauderdale, FL (US)

( * ) Notice: Subject to any disclaimer, the term of this patent is extended or adjusted under 35 U.S.C. 154(b) by 54 days.

(21) Appl. No.: 12/779,767

(22) Filed: May 13, 2010

(65) Prior Publication Data

US 2011/0125251 A1    May 26, 2011

Related U.S. Application Data

(60) Provisional application No. 61/223,435, filed on Jul. 7, 2009, provisional application No. 61/178,139, filed on May 14, 2009.

(51) Int. Cl.
  *A61F 2/82*  (2013.01)
  *A61F 2/91*  (2013.01)
  *A61F 2/88*  (2006.01)
  *A61F 2/915*  (2013.01)

(52) U.S. Cl.
  CPC . *A61F 2/91* (2013.01); *A61F 2/88* (2013.01); *A61F 2/915* (2013.01); *A61F 2002/91508* (2013.01); *A61F 2002/91516* (2013.01); *A61F 2002/91525* (2013.01); *A61F 2002/91558* (2013.01); *A61F 2250/0039* (2013.01)

(58) Field of Classification Search
  CPC .. A61F 2/91; A61F 2/915; A61F 2002/91516; A61F 2002/91525; A61F 2002/91508; A61F 2250/0039
  USPC ...... 606/200; 623/1.15, 1.16, 1.18, 1.2, 1.22
  See application file for complete search history.

(56) References Cited

U.S. PATENT DOCUMENTS

| | | | |
|---|---|---|---|
| 5,354,308 A | 10/1994 | Simon | |
| 5,868,781 A * | 2/1999 | Killion | 623/1.15 |
| 5,879,381 A | 3/1999 | Moriuchi | |
| 5,891,191 A | 4/1999 | Stinson | |
| 5,968,093 A | 10/1999 | Kranz | |
| 6,013,854 A | 1/2000 | Moriuchi | |
| 6,020,385 A | 2/2000 | Halle | |
| 6,117,165 A | 9/2000 | Becker | |

(Continued)

FOREIGN PATENT DOCUMENTS

EP    0401844    6/1990

OTHER PUBLICATIONS

PCT/US10/34795, International Search Report dated Jul. 8, 2010.
(Continued)

*Primary Examiner* — Darwin Erezo
*Assistant Examiner* — Anh Dang
(74) *Attorney, Agent, or Firm* — Leason Ellis LLP

(57) ABSTRACT

The self-expanding stent of the present invention provides for a transition zone between the main body of the stent and the end zone, comprising a plurality of n-sided polygons where the surface area of the adjacent polygons in the transition zone is unequal. In one embodiment, the surface area of the polygons in the transition zone increases circumferentially across the transition zone in a clockwise or counterclockwise manner. The polygons are formed from two pairs of undulations which are connected by segments. The bending moment of the undulations is equal within each polygon and constant across the transition zone.

20 Claims, 32 Drawing Sheets

(56) References Cited

U.S. PATENT DOCUMENTS

| | | | |
|---|---|---|---|
| 6,168,617 B1 | 1/2001 | Blaeser | |
| 6,222,097 B1 | 4/2001 | McBride | |
| 6,331,186 B1 | 12/2001 | Wang | |
| 6,478,814 B2 | 11/2002 | Wang | |
| 6,497,729 B1 | 12/2002 | Moussy | |
| 6,551,351 B2 | 4/2003 | Smith | |
| 6,607,548 B2 | 8/2003 | Pohjonen | |
| 6,696,402 B2 | 2/2004 | Gosselink | |
| 6,706,854 B2 | 3/2004 | Buchholz | |
| 6,838,528 B2 | 1/2005 | Zhao | |
| 6,878,162 B2 * | 4/2005 | Bales et al. | 623/1.15 |
| 6,897,205 B2 | 5/2005 | Beckert | |
| 6,969,402 B2 | 11/2005 | Bales | |
| 7,037,772 B2 | 5/2006 | Yeo | |
| 7,169,162 B2 | 1/2007 | Garakani | |
| 7,169,175 B2 | 1/2007 | Cottone | |
| 7,300,458 B2 | 11/2007 | Henkes | |
| 7,329,277 B2 | 2/2008 | Addonizio | |
| 7,988,723 B2 | 8/2011 | Beach et al. | |
| 2002/0095208 A1 * | 7/2002 | Gregorich et al. | 623/1.15 |
| 2003/0149473 A1 * | 8/2003 | Chouinard et al. | 623/1.15 |
| 2004/0034402 A1 * | 2/2004 | Bales et al. | 623/1.2 |
| 2004/0199244 A1 | 10/2004 | Ballou | |
| 2006/0121012 A1 | 6/2006 | Kutryk | |
| 2006/0135476 A1 | 6/2006 | Kutryk | |
| 2006/0247759 A1 * | 11/2006 | Burpee | A61F 2/88 623/1.15 |
| 2006/0271158 A1 | 11/2006 | Olson | |
| 2007/0042017 A1 | 2/2007 | Kutryk | |
| 2007/0055367 A1 | 3/2007 | Kutryk | |
| 2007/0141107 A1 | 6/2007 | Kutryk | |
| 2007/0156232 A1 | 7/2007 | Kutryk | |
| 2007/0191932 A1 | 8/2007 | Kutryk | |
| 2007/0196422 A1 | 8/2007 | Kutryk | |
| 2007/0213801 A1 | 9/2007 | Kutryk | |
| 2008/0004690 A1 * | 1/2008 | Robaina | 623/1.15 |
| 2008/0086197 A1 | 4/2008 | Gregorich et al. | |
| 2008/0319534 A1 * | 12/2008 | Birdsall et al. | 623/1.22 |
| 2009/0036976 A1 * | 2/2009 | Beach et al. | 623/1.22 |
| 2010/0093946 A1 | 4/2010 | Thatcher | |
| 2011/0004290 A1 * | 1/2011 | Bales, Jr. | A61F 2/88 623/1.16 |

OTHER PUBLICATIONS

NiTi Memory Metal. University of Wisconsin [online]. Retrieved from the Internet <http://mrsec.wisc.edu/Edetc/cineplex/NiTi/index.html>.
Shape Memory Alloy. Wikipedia [online]. Retrieved from the Internet <http://en.wikipedia.org/wiki/Shape_memory_alloy>.
MSI Stent Crimping Equipment. Machine Solutions [online]. Retrieved from the Internet <http://www.machinesolutions.org/stent_crimping.htm>.
Polygon Area. Wolfram Math World [online]. Retrieved from the Internet <http//:mathworld.wolfram.com/PolygonArea.html>.
Curved Beams. Roymech U.K. [online]. Retrieved from the Internet <http//:www.roymech.co.uk/Useful_Tables/Beams/Curved_beams.html>.
Mechanics of Materials Laboratory. University of Washington [online]. Retrieved from the Internet <http//:courses.washington.edu/mengr354/jenkins/notes354.html>.
Stent Research Unit—Finite Element Analysis of stents. Universiteit Gent [online]. Retrieved from the Internet <http//:www.stent-ibitech.ugent.be/research/fea.htm>.
Better Bloodflow with Low-Stress Stent. MSC Software [online]. Retrieved from the Internet <http//:www.mscsoftware.com/success/details.cfm?Q=286&sid=352>.
A survey of stent designs. EuroFlex [online]. Retrieved from the Internet <www.euroflex-gmbh.de/pdfs/stentdesign.pdf>.
Surface Area Equation and Calculation Menu. Engineers Edge [online]. Retrieved from the Internet <http//:www.engineersedge.com/area_properties/area_calc_menu.shtml>.
Pierce Protein Research Products. Thermo Scientific [online]. Retrieved from the Internet <http//:www.piercenet.com/products/browse.cfm?fldID=020306>.
Jeon, et al. "Synthesis and Characterization of Poly (L-lactide)—Poly (e-caprolactone) Multiblock Copolymers," Macromolecules. 2003, vol. 36; pp. 5585-5592.
International Search Report and Written Opinion for international application No. PCT/US2010/034795 issued by the International Searching Authority mailed on Jul. 8, 2010.

* cited by examiner

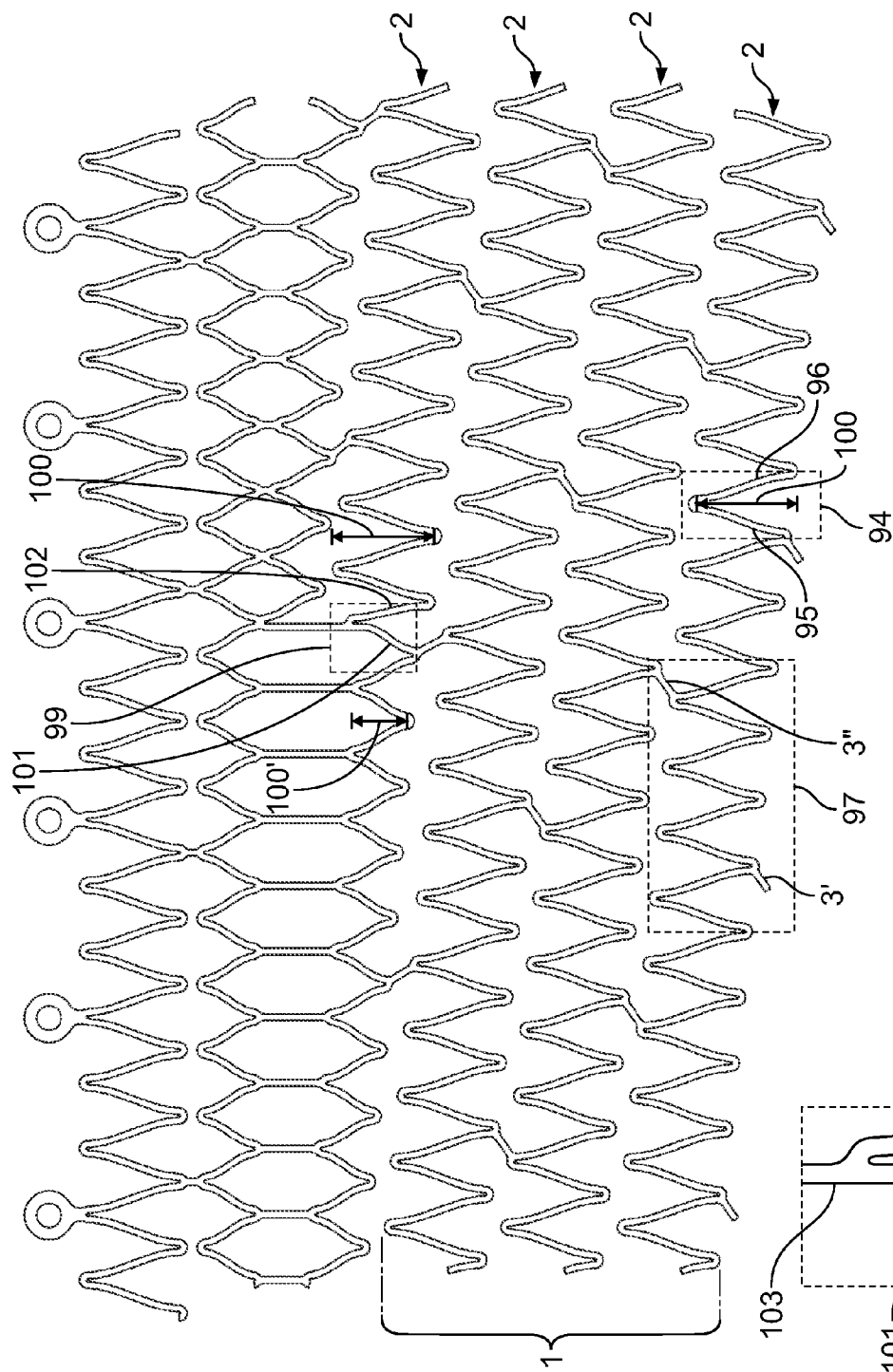

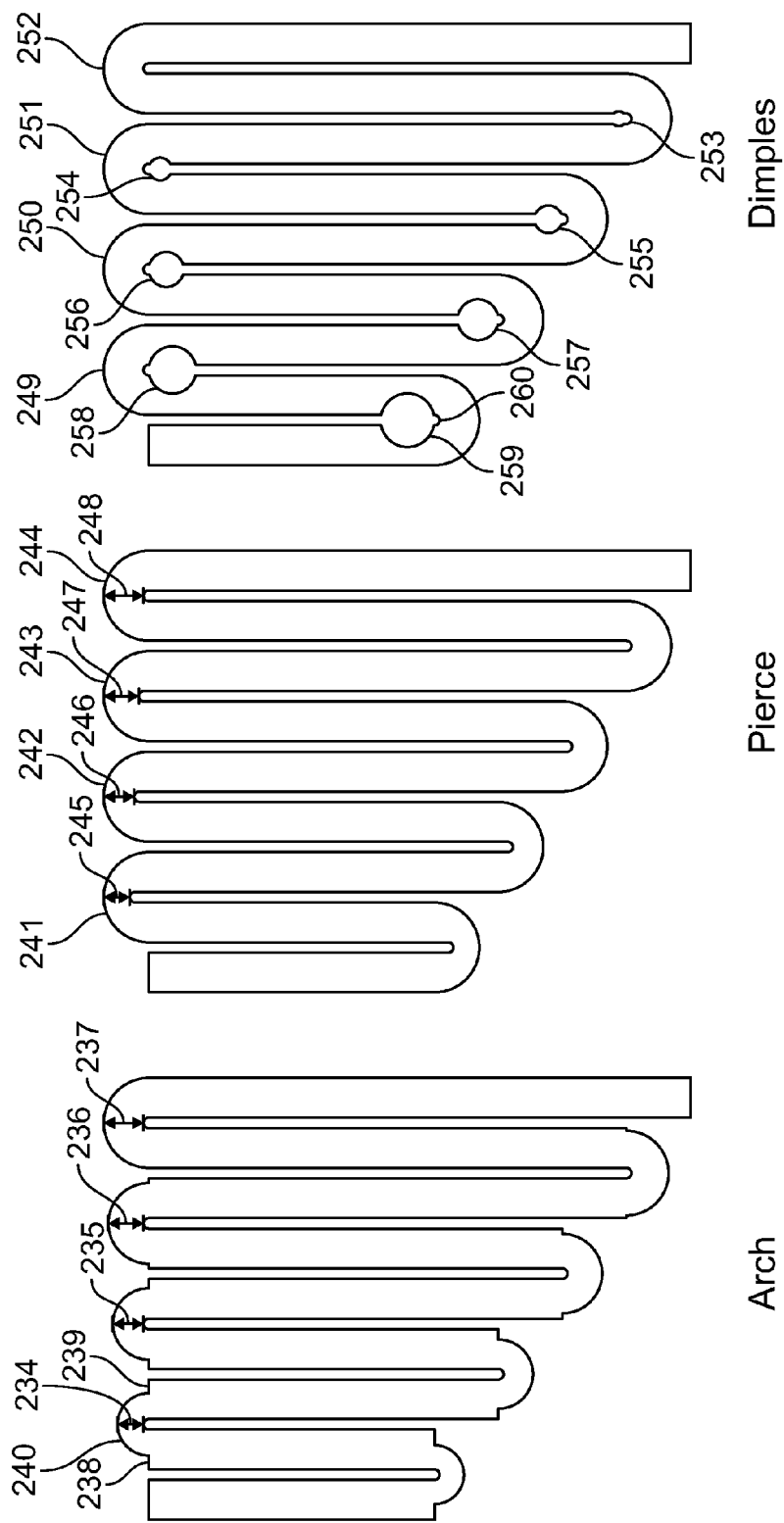

SELF-EXPANDING STENT WITH POLYGON TRANSITION ZONE

CROSS-REFERENCE RELATED APPLICATIONS

This application claims the benefit of U.S. Provisional Application No. 61/178,139 filed May 14, 2009, and U.S. Provisional Application No. 61/223,435 filed Jul. 7, 2009

BACKGROUND OF THE INVENTION

Stents are scaffolds which are positioned in diseased vessel segments to support the vessel walls. During angioplasty, stents are used to repair and reconstruct blood vessels. Placement of a stent in the affected arterial segment prevents elastic recoil and closing of the artery. Stents also prevent local dissection of the artery along the medial layer. Physiologically, stents may be placed inside the lumen of any space, such as an artery, vein, bile duct, urinary tract, alimentary tract, tracheobronchial tree, cerebral aqueduct or genitourinary stent. Stents may also be placed inside the lumen of non-human animals, such as primates, horses, cows, pigs and sheep.

In general, there are two types of stents: self-expanding and balloon-expandable. The balloon-expandable stent is placed in a diseased segment of a vessel by inserting an unexpanded stent into the affected area within the vessel. Prior to insertion, the stent is crimped onto a balloon which is inflated to expand the stent against the vessel wall. Inflation remodels the arterial plaque and secures the stent within the affected vessel. Balloon expandable stents may suffer from the collapse as a result of the natural elastic recoil of the vessel wall and lack of resilience of the stent itself.

Self-expanding stents are capable of expanding by themselves. There are many different designs of self-expanding stents, including helical, circular, cylinder, roll, stepped-pipe, high-order coil, braided wire, cage or mesh.

Self-expanding stents may be formed from super-elastic or shape memory metal. U.S. Pat. No. 6,013,854. In stents, nickel-titanium (NiTi) alloys are commonly used. http://mrsec.wisc.edu/Edetc/cineplex/NiTi/indexhtml, April, 2009. Stents formed from NiTi alloys are highly resilient, even when compressed because of the superelastic properties of the alloy. When cooled below the transformation temperature such as by liquid nitrogen, the NiTi alloy transforms to a martensite phase, holding a new shape until it warms back-up. This transformation can be referred to as a change between a martensite phase (stable at low temperatures) and an austenite phase (stable at high temperatures). http://en.wikipedia.org/wiki/Shape_memory_alloy, April, 2009.

The self-expanding stent is placed in the vessel by inserting the stent in a compressed state into the affected region, e.g., an area of stenosis. Compression or crimping of the stent can be achieved using crimping equipment (see, http://www.machinesolutions.org/stent_crimping.htm, April, 2009). The stent may also be compressed using a tube that has a smaller outside diameter than the inner diameter of the affected vessel region. Once the compressive force is removed or the temperature raised, the stent expands to fill the lumen of the vessel. When the stent is released from confinement in the tube, the stent expands to resume its original shape, in the process becoming securely fixed inside the vessel against the wall.

Each of the various stent designs that have been used with self-expanding stents has certain functional problems. For example, because the helical windings forming the stent terminate unevenly, the last portion of winding expands at a different rate from other areas in the stent. This problem, differential expansion, may be solved, in part, by introducing a transition zone between the main body of the stent and the end zone. See, e.g., U.S. Pat. Nos. 6,878,162, 6,969,402 and 7,169,175 for examples of various transition zones. However, because the transition zone joins two different, structural segments of the stent, an end zone on one side and a main body or helical portion on the other, the strut lengths of the transition zone vary. Such a variation can result in a change in stress or bending moment of the stent across the transition zone. This lack of uniformity affects the ability of the stent to be uniformly compressed and expanded which in turn impacts insertion of the stent into a convoluted vessel. Accordingly, there is a need to develop geometric designs which allow for uniform expansion across the transition zone, while still permitting maximal flexibility.

The present invention provides a geometric design for a stent that has both a high degree of flexibility and significant radial strength as well as provides for uniform expansion across the transition zone. The design of this stent also allows it to be inserted into small diameter vessels having complex geometry. The stent is further capable of responding dynamically to changes in blood pressure.

SUMMARY OF THE INVENTION

The self-expanding stent of the present invention provides for a transition zone between the main body of the stent and the end zone, comprising a plurality of n-sided polygons where the surface area of the adjacent polygons in the transition zone increases circumferentially. The surface area of the polygons in the transition zone increases circumferentially across the transition zone in a clockwise or counterclockwise manner. The polygons are formed from two pairs of undulations which are connected by segments. The bending moment M of the undulations is equal within each polygon and constant across the transition zone.

The stent comprises: a main body formed from a plurality of first cylindrical windings where adjacent first cylindrical windings are connected by at least one first strut and a transition zone disposed at either end of the main body. The transition zone comprises a plurality polygons having increasing surface area across the transition zone and the polygons of the transition zone are connected to the main body by at least one second strut. Adjacent polygons may have unequal surface areas. The surface area of the polygons can increase in a clockwise or counter clockwise manner. In a crimped configuration, opposite sides in each polygon are substantially parallel to each other in a crimped configuration. The stent may contain an end zone disposed at either end of the main body, where the end zone is attached to the transition zone by at least one third strut. The end zone comprises at least one second cylindrical winding and may further comprise at least one radiopaque marker. The first cylindrical windings propagate helically.

The polygons may comprise hexagons, where each hexagon is formed from a first undulation and second undulation connected by a first and second segments. The first and second undulations in each hexagon may have the same thickness, width and length. The surface area of the hexagons across the transition zone increases in a clockwise or counter clockwise manner across the transition zone relative the long axis of the stent. The bending moment of the first undulation and second undulation in each hexagon in the transition zone are equal and remain constant across hexagons of the transition zone. In one embodiment, the polygon is an even sided polygon and can comprise a 4, 6, 8, 10, 12, 14, 16, 18, 20, 22, 24, 26, 28 and 30 sided polygons. Higher sided polygons are also encompassed by the designs of the present invention.

The first cylindrical windings comprise a plurality of third undulations, where each third undulation comprises a two segments, labeled in some embodiments as the third and fourth segments. The number of segments between any two first struts may be 3, 5, 6, 7, 8 or 9. The first cylindrical windings many propagate helically.

The stent of the present invention may comprise: a main body formed from a plurality of first cylindrical windings where adjacent cylindrical windings are connected by at least one first strut; a transition zone disposed at either end of the main body, where the transition zone comprises a plurality of first and second undulations, the first and undulations are connected by at least two segments, wherein the plurality of second undulations propagate helically and the plurality of first undulations propagate circumferentially. The second undulations are connected to the first cylindrical windings by at least one second strut. The stent may further comprise an end zone disposed at either end of the main body, where the end zone is attached to the transition zone by at least one third strut. The end zone comprises at least one second cylindrical windings. The stent may further comprise at least one radiopaque marker on the end zones.

The stent may also comprise: a main body formed from a plurality of first cylindrical windings where adjacent cylindrical elements are connected by at least one first strut; a transition zone disposed at either end of the main body. The length of a first segment may be greater than the length of a second segment. The transition zone comprises at least one polygon formed by the first segment, a second segment, at least one first undulation and at least one second undulation. The segments may be linear or curvilinear.

In another embodiment, the stent of the present invention also comprises: a main body formed from a plurality of cylindrical windings wherein adjacent cylindrical windings are connected by at least one first strut and a transition zone disposed at either end of the main body. The transition zone comprises a plurality of undulations, each undulation comprising two adjacent second struts connected by a loop and where the width of the loop varies across the transition zone. Adjacent loops may have unequal widths. The width of the loops can increase clockwise or counterclockwise relative to the long axis of the stent. The stent may have an end zone disposed at either end of the main body. The end zone is attached to the transition zone by at least strut. The end zone comprises at least one second cylindrical winding and may have least one radiopaque marker.

The first cylindrical windings may propagate helically

In one embodiment, the loops may further comprise a hole positioned in the loop. Adjacent holes may have unequal surface areas. The surface area of the hole may increase in a clockwise or counterclockwise manner relative to the long axis of the stent.

The bending moment of each loop in the transition zone is equal.

The first cylindrical windings comprise a plurality of third undulations; each third undulation comprises two segments. The two segments may be linear or curvilinear. The number of segments between two first struts is selected from the group consisting of 3, 5, 6, 7, 8, 9 and 10. The cylindrical windings propagate helically.

The stent may also comprise: a main body formed from a plurality of first cylindrical windings wherein adjacent cylindrical windings are connected by at least one first strut and a transition zone disposed at either end of the main body. The transition zone comprises a plurality of undulations, each undulation comprising two adjacent second struts connected by a loop comprising a hole, where the width of the loop varies across the transition zone and where the surface area of the hole and width of the loop vary inversely.

BRIEF DESCRIPTION OF THE DRAWINGS

FIG. 9a13 A 10-sided polygon transition zone in an expanded configuration.
FIG. 9b—A 10-sided polygon transition zone in a crimped configuration.
FIGS. 11a-c—Crimped and expanded views of one embodiment of the stent, including a close-up view of the junction zone.

DETAILED DESCRIPTION

The self-expanding stent of the present invention provides for a transition zone between the main body of the stent and the end zone, comprising a plurality of n-sided polygons where the surface area of adjacent polygons in the transition zone is unequal. In one embodiment, the surface area of the polygons in the transition zone increases circumferentially across the transition zone around the long axis of the stent in a clockwise or counterclockwise manner. The polygons are formed from two pairs of undulations which are connected by a plurality of segments. The bending moment M of the undulations is equal within each polygon and remains constant across the transition zone, although the specific bending moment M depends on the length, thickness and width of the various segments forming each undulation.

The stent may be inserted into the lumen of any vessel or body cavity expanding its cross-sectional lumen. The invention may be deployed in any artery, vein, duct or other vessel such as a ureter or urethra and may be used to treat narrowing or stenosis of any artery, including, the coronary, infrainguinal, aortoiliac, subclavian, mesenteric or renal arteries.

Figure 1:
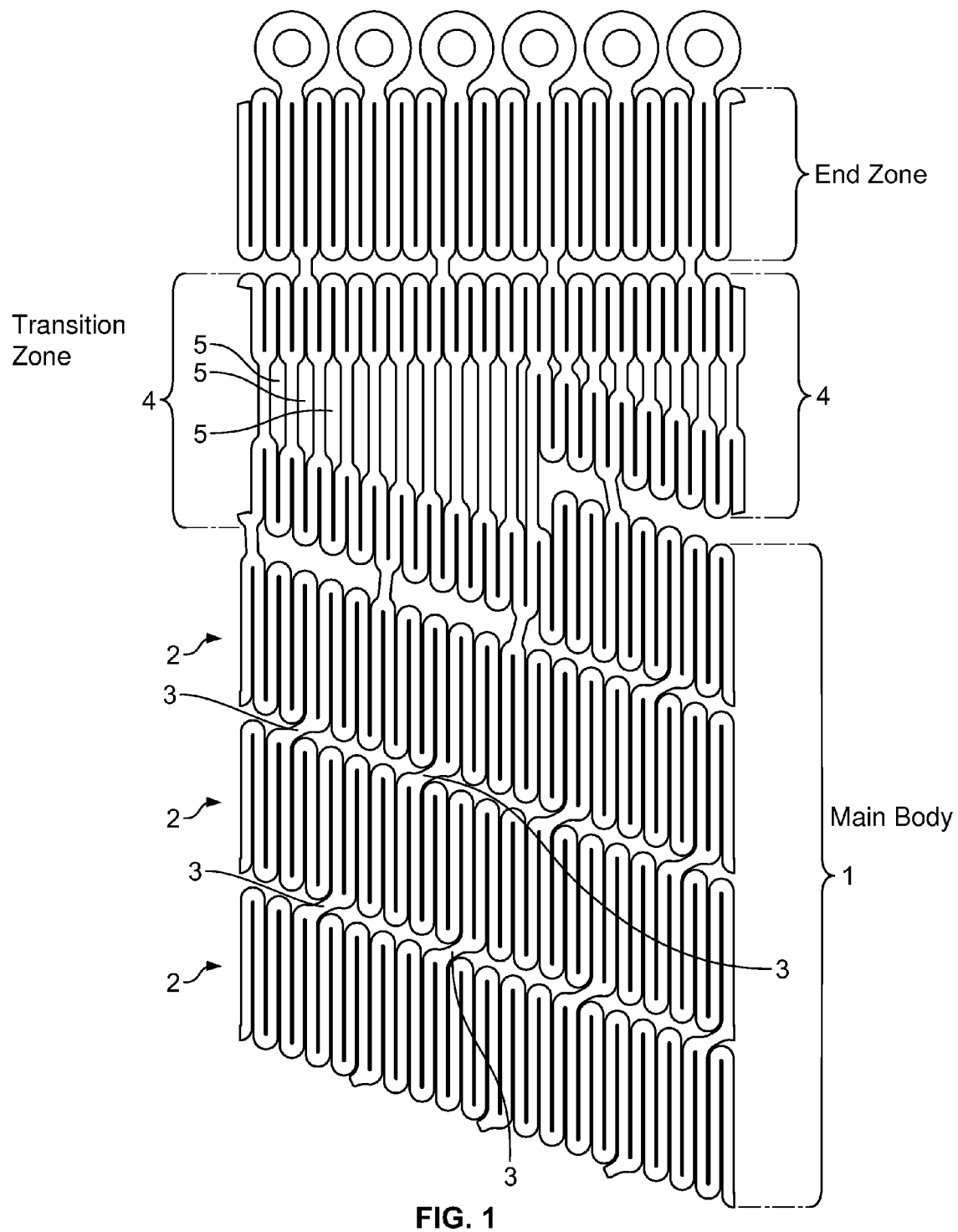
FIG. 1—The stent in a crimped configuration.
Figure 2:
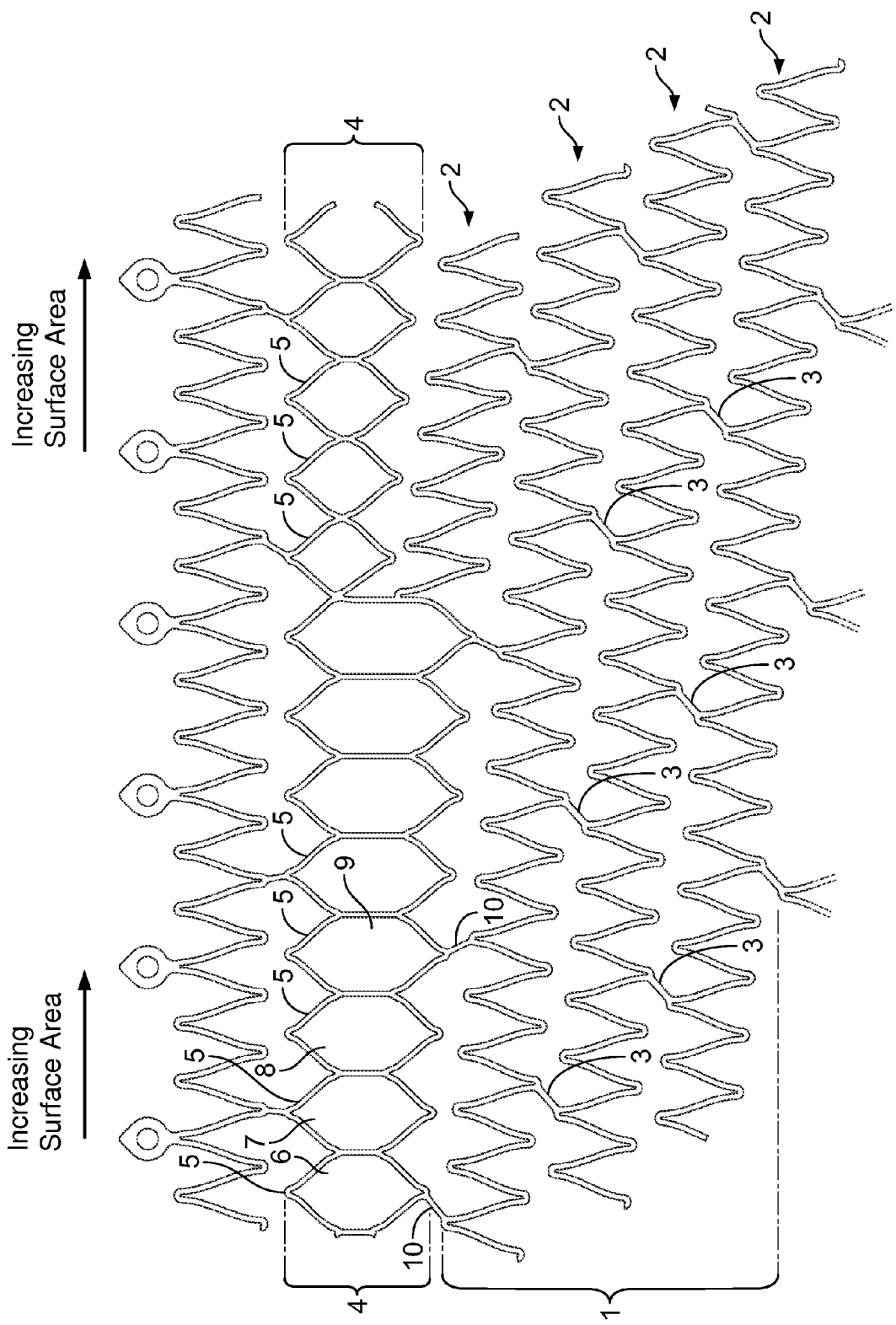
FIG. 2—The stent in an expanded configuration.

FIGS. 1 and 2 show flat images of one embodiment of the stent in a crimped, FIG. 1, and expanded, FIG. 2, state. The polygons in this embodiment are shown as hexagons; however, the polygons may have an even number sides ranging from 4 to 30 (higher order polygons are encompassed by the designs of the present invention). The stent comprises a main body 1 which comprises cylindrical windings 2. Adjacent cylindrical windings 2 are connected by at least one first strut 3. The first struts may assume a variety of angles relative to the long axis of the stent, including, 0-20°, 20-40° and 40-60° (the angle of these struts may be positive or negative relative to the long axis of the stent).

The stent comprises a transition zone 4 formed from a plurality of polygons 5. The surface area of the polygons, as exemplified by the hexagons shown as 6, 7, 8, 9 in FIG. 2, increases across the transition zone in a circumferential manner relative to the long axis of the stent. In one embodiment, the surface area of adjacent polygons is unequal, but embodiments where adjacent groups of polygons have equal surface areas are also possible. The polygons of the transition zone 4 are connected to the main body 1 by at least one second strut 10.

Although the polygons are shown as hexagons in FIG. 2, the polygons can comprise an even number, e.g., 4, 6, 8, 10, 12, 14, 16, 18, 20, 22, 24, 26, 28 and 30 sided polygons, up to an n-sided polygon. The sides of the polygons may be equal or unequal. The surface area of the polygons, i.e., the area encompassed by the sides, can be calculated mathematically from the length of the sides of the polygon. http://mathworld.wolfram.com/PolygonArea.html, April, 2009.

Figure 3:
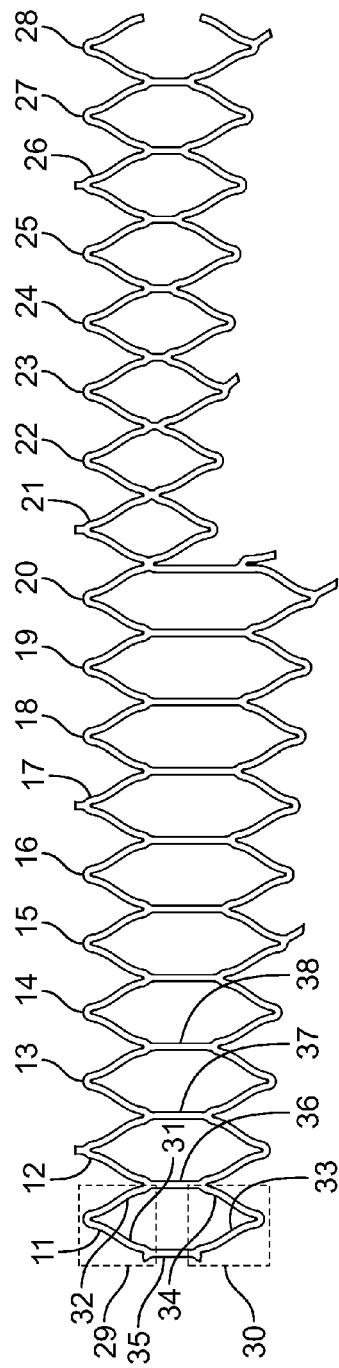
FIG. 3—The transition zone of FIG. 2.

In FIG. 3, each hexagon 11-28 of the transition zone 4, comprises two undulations, a first undulation 29 and a second undulation 30 (for clarity of illustration, only selected undulations are labeled, although each hexagon contains an undulation). The undulations are formed from segments, which include, 31, 32 (first undulation 29) and 33, 34 (second undulation 30). The segments of the undulations, 31, 32, 33, and 34, may be linear or curvilinear; the segments of the undulations may also comprise bends that are placed at selected points along their length. The length, width and thickness of the segments of the undulations, 31, 32, 33 and 34, may be equal or unequal. The first 29 and second 30 undulations of each hexagon 11-28 across the transition zone may be identical.

The first undulation 29 and the second undulation 30 are connected by a first 35 and second 36 segment (note for the sake of clarity, only segments in a selected group of polygons are illustrated). Because the hexagons form a continuous, interconnected structure across the transition zone, it will be appreciated that each adjacent hexagon shares both the first 35 and second 36 segments and that the designation of first and second segments are for illustration purposes only. Additional segments are shown as 36, 37, and 38 for example. The first and second segments of polygon 12 are 36 and 37 respectively and the first segment of polygon 13 is 37, which is the second segment of polygon 12 and so forth. The first 35 and second 36 segments may be linear or curvilinear; the segments may also comprise bends that may be placed at selected points along their length. The length of the first 35 and second 36 segments varies across the transition zone. In FIG. 3, the rank order of the lengths of the segments is 35<36<37<38. Various embodiments of these segments are illustrated below. The length, width and thickness of the first 35 and second 36 segments may be equal to the length, width and thickness of the segments forming the undulations 31, 32, 33 and 34. It should be noted that in one embodiment, the length of the segments connecting the first undulation 29 and second undulation 30 may be zero; in other words, the two undulations may be directly connected, forming a 4-sided polygon. For example, in a four-sided polygon, the first undulation 29 and second undulation 30 may be directly connected to each other.

Figure 4A:
FIGS. 4a and 4b—A close-up of the undulation of the polygon from FIG. 3.
Figure 4B:
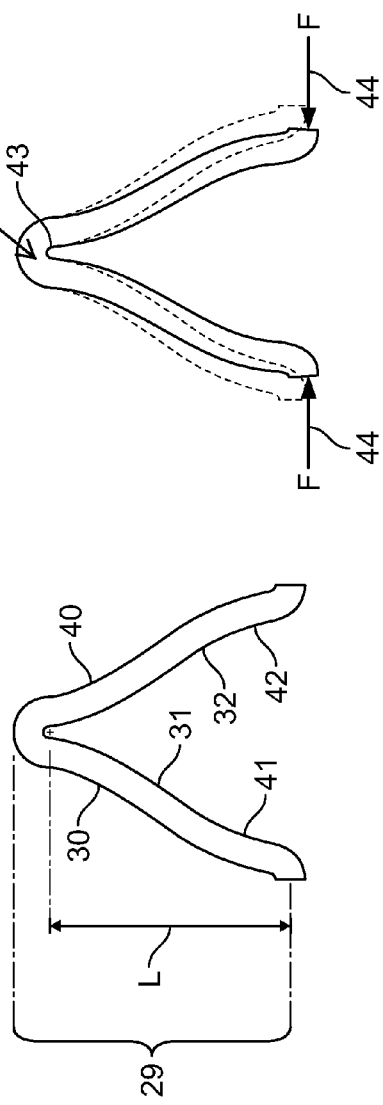

The structure of one embodiment of the first 29 and second 30 undulations is shown in greater detail in FIG. 4a. Because the first 29 and second 30 undulations have identical dimensions, only the movement of the first undulation 29 will be considered as the second undulation will behave in a similar manner. The segments 31 and 32 of the first undulation 29 may be straight or curvilinear. A curvilinear embodiment is shown in FIG. 4 where the segments 31 and 32 show concave 39, 40 and convex 41,42 curvature along portions of the segments. The degree of curvature may vary. When the segments 31, 32 are crimped (shown diagrammatically by the application of force, F (44)), the bending moment, M, is measured at 40. The bending moment M 43 is calculated as: $M=F(L+r_n)$, where F, 44, is the force applied, L is the length of the segments 31,32, and $r_n$ is the neutral radius where there is zero stress or strain along the curved or bent portion. See, http://www.roymech.co.uk/Useful_Tables/Beams/Curved_beams.html (April, 2009), http.//courses.washington.edu/mengr354/jenkins/notes354.html (April, 2009) for calculations of stress, strain and bending moments in curved beams.

Figure 5A:
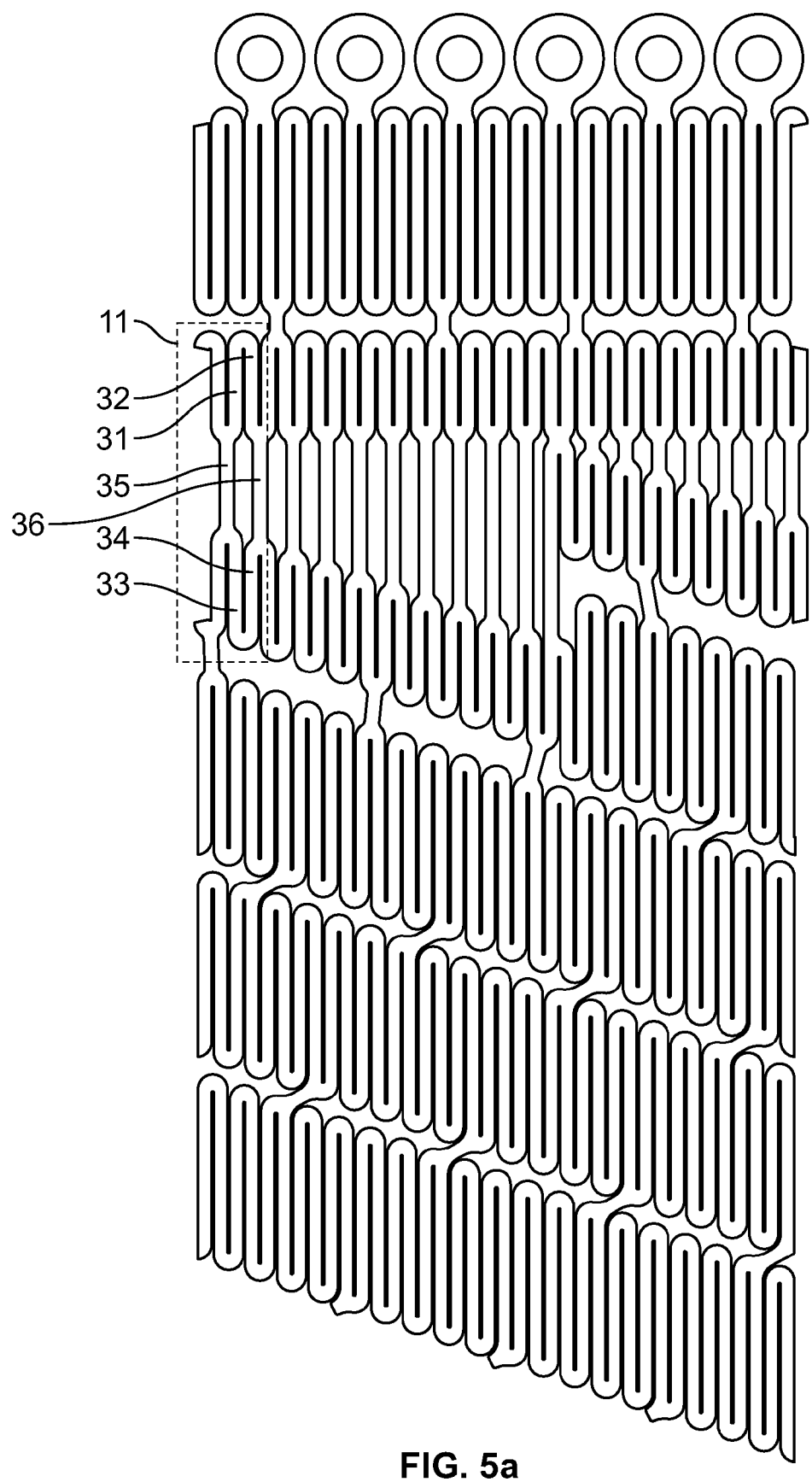
FIG. 5a—The stent in a crimped configuration.
Figure 5B:
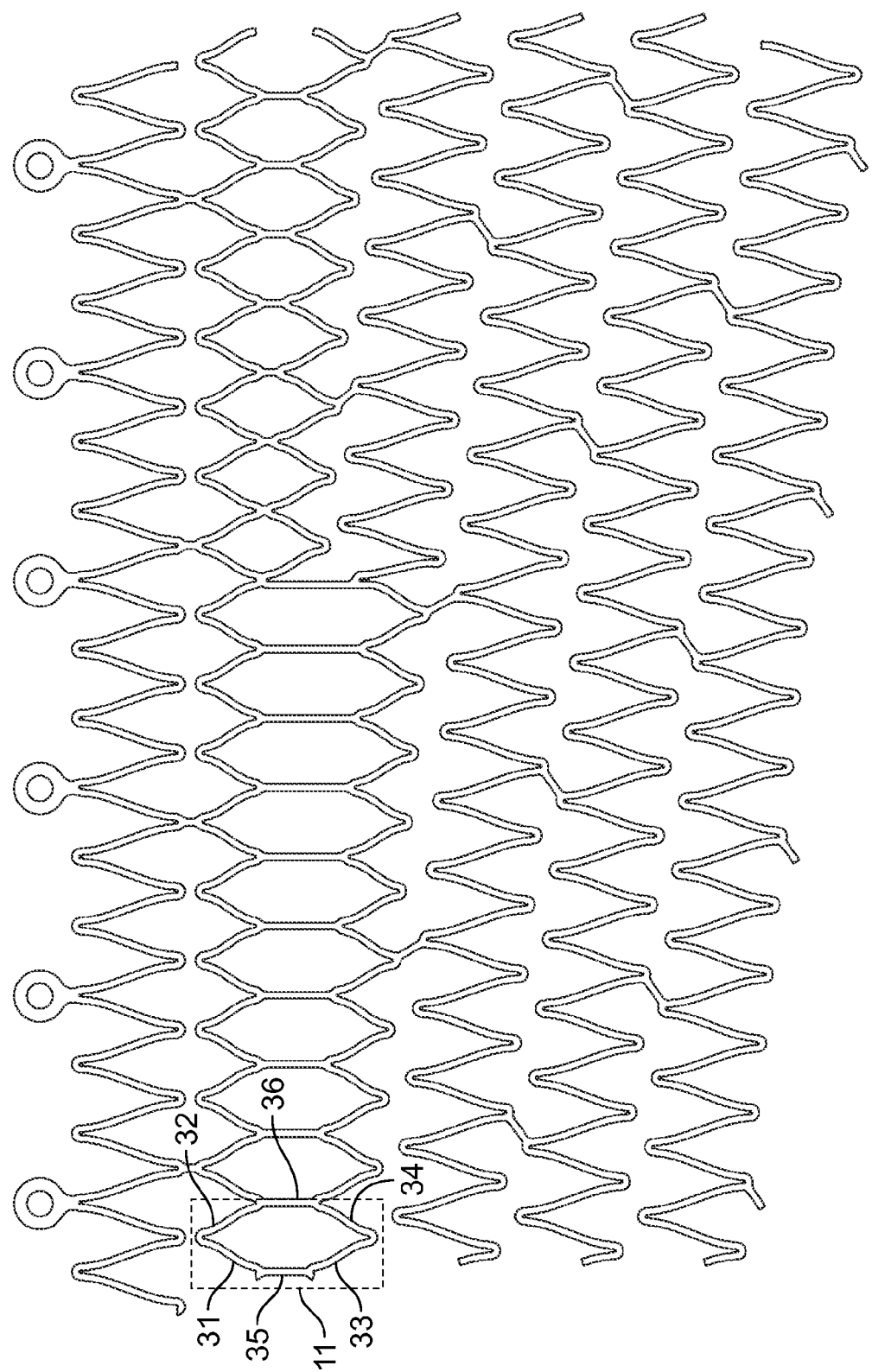
FIG. 5b—The stent in FIG. 5a in an expanded configuration (note the diameter of the stent is different from seen in FIG. 2).
Figure 5C:
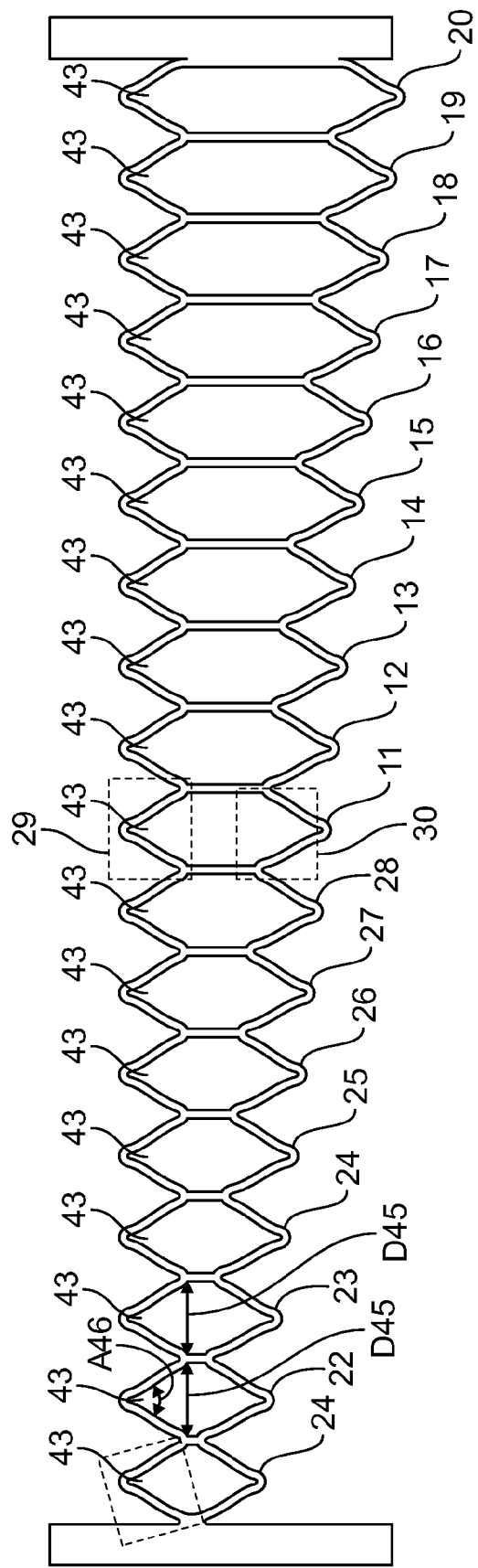
FIG. 5c—An FEA Analysis of a 6-sided polygon.

The stent of the present invention is delivered via a catheter in a crimped configuration. The self-expanding stent is placed in the vessel by inserting the stent in a compressed state into the affected region, e.g., an area of stenosis. Once the compressive force is removed (or alternatively, the temperature raised), the stent expands to fill the lumen of the vessel. The stent may be compressed using a tube that has a smaller outside diameter than the inner diameter of the affected vessel region. When the stent is released from confinement in the tube, the stent expands to resume its original shape, in the process becoming securely fixed inside the vessel against the wall. FIG. 5a shows the stent in a crimped configuration. For illustration purposes, the behavior of a single polygon 11 is considered; however, all polygons across the transition zone behave in a similar manner in both a crimped and expanded configuration. In a crimped configuration (FIG. 5a), the opposite or opposing sides of the polygon 11 are substantially parallel to each other. Specifically, note elements 31,32, elements 35,36 and 33,34. As used herein, substantially parallel means that opposite or opposing sides in a polygon form non-intersecting lines over their entire length. The stent in an expanded configuration is shown in FIG. 5b. Empirically, the bending moment M 43 may be measured by finite element analysis, (FEA). Application of FEA analysis to stents is well known in the art and provides both a numerical and visual representation of stress and strain across the body of the stent.

htpp://www.stent-ibitech.ugent.be/research/fea.htm, April 2009. Software for FEA analysis is commercially available (http://www.mscsoftware.com/success/details.cfm?Q=286&sid=352, April, 2009). The following FEA analysis shows that the bending moment M 43 of each undulation in the transition zone remains constant across the transition zone 4. FIG. 5c. In addition, the bending moments of the first 29 and second 30 undulations are equal. Thus, the geometry of the stent design allows for a constant bending moment, opening distance D 45 and opening angle A 46 across the transition zone as the stent expands. It is noted, that although the first 29 and second undulations 30 are only noted for one polygon 11, the above description of the bending moment M 43 applies equally for all polygons 11-20 and 21-28 across the entire transition zone 4.

In higher-order polygons, e.g., n=8-30, the undulations are connected by a plurality of segments; however, the undulations across the transition zone 4 are equal in dimension, i.e., the segments comprising the undulations have equal length, width and thickness, allowing for the bending moment 43 to remain constant both within one polygon and across the plurality of polygons in the transition zone 4.

Figure 6:
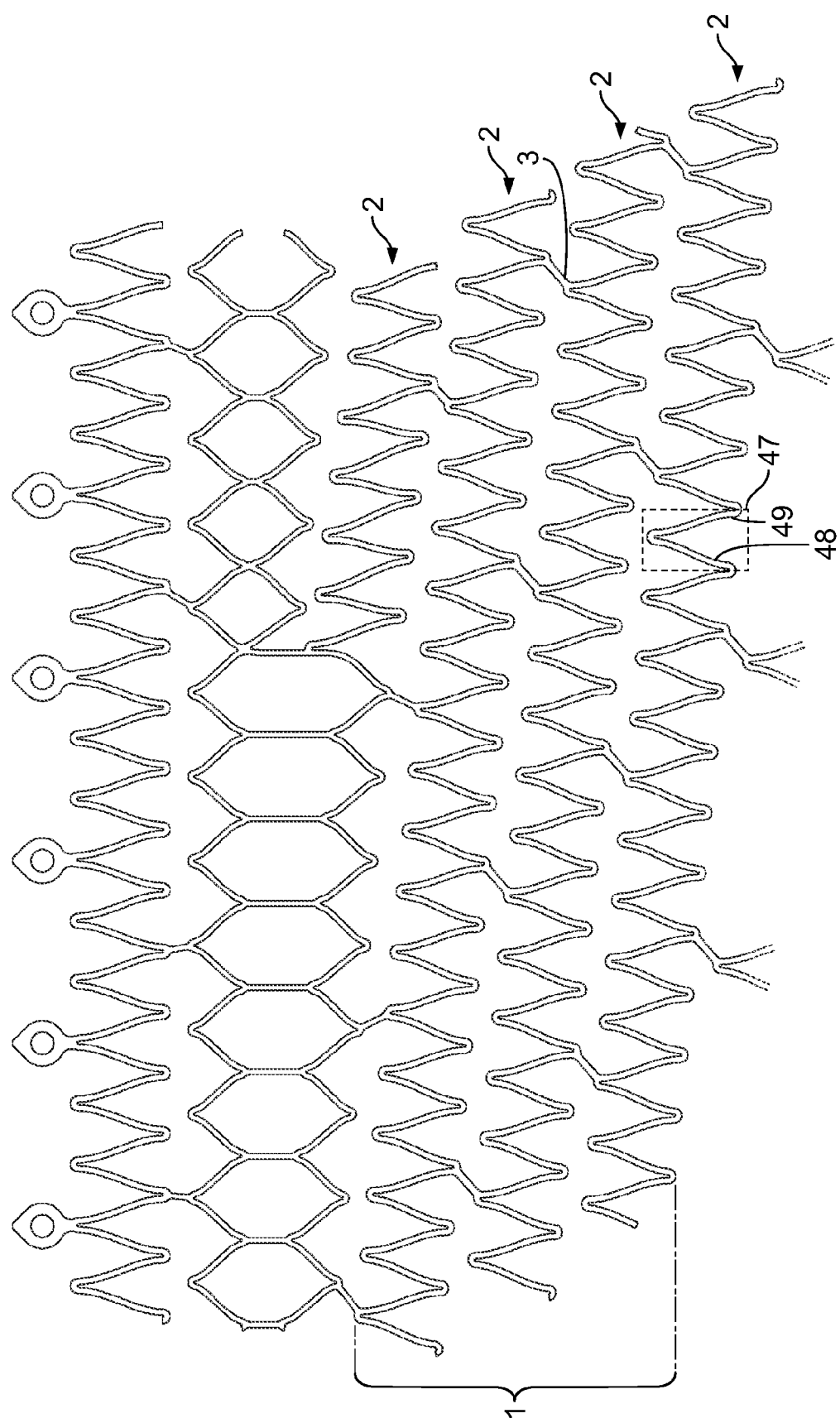
FIG. 6—The main body of the stent.
Figure 7:
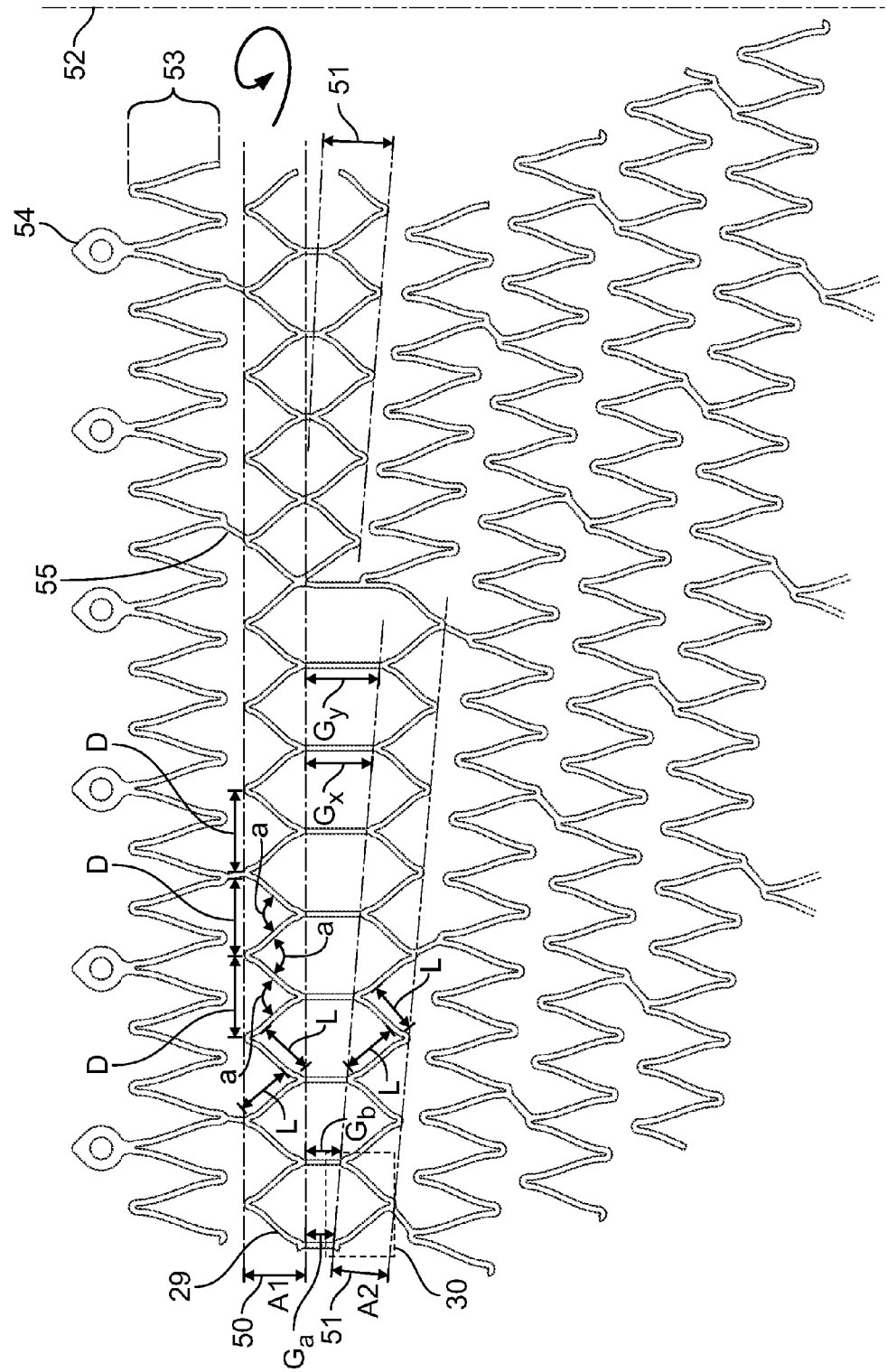
FIG. 7—The transition zone and end zone.

The main body of the stent 1 may comprise a first cylindrical winding which comprises a plurality of third undulations 47 (for clarity, only a single undulation is highlighted in FIG. 6a). The third undulation 47 is comprised of two segments referred to here as a third 48 and fourth 49 segments. The third 48 and fourth 49 segments may be linear or curvilinear and may have bends positioned along their length. The third 48 and fourth 49 segments may be equal in length. The length of these segments may vary from about 0.5 mm to about 3 mm, from about 1.0 mm to about 2.5 mm, from about 1.5 mm to about 2.0 mm and in one embodiment about 1.68 mm. The cylindrical winding 2 may propagate helically, U.S. Pat. No. 7,169,175 or may comprise a series of circumferential elements as described in U.S. Pat. No. 7,329,277. The third undulations in adjacent helical turns may be connected by at least one first strut 3. The number of first struts 3 in each helical turn may vary (see below for discussion of other embodiments). The first struts may assume a variety of angles relative to the long axis of the stent, including, 0-20°, 20-40° and 40-60° (the angle of these struts may be positive or negative relative to the long axis of the stent). The struts 3 may have the same or different angles with respect to one another. The width and thickness of the cylindrical windings varies, but may be equal to the width and thickness of the first 35 and second 36 segments or the width and thickness of the segments of the undulations 31, 32, 33 and 34. For example, the width may vary from about 0.05 mm to about 0.2 mm, from about 0.075 mm to about 0.15 mm, from about 0.1 mm to about 0.130 mm and in one embodiment about 0.123 mm after electropolishing. The thickness may vary from about 0.05 mm to about 0.3 mm, from about 0.1 mm to about 0.25 mm, from about 0.15 mm to about 0.20 mm and in one embodiment about 0.19 mm. The length of the third 48 and fourth 49 segments may be equal and may be constant across the entire main body 1.

Figure 8:
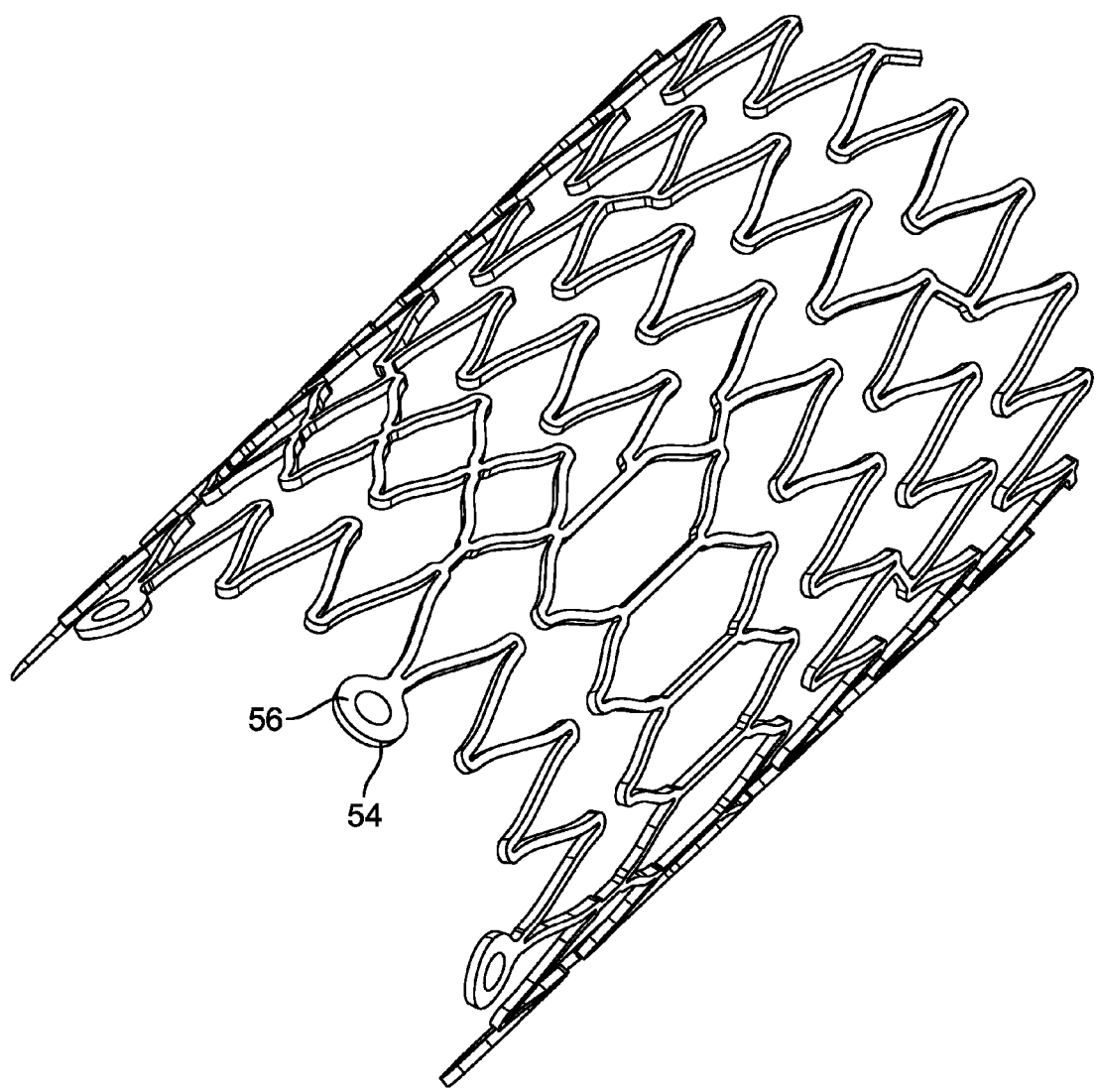
FIG. 8—The radiopaque marker for placement.

In addition, to viewing the transition zone 4 as comprising a plurality of polygons, the transition zone 4 may comprise a plurality of first undulations 29 propagating in a circumferential direction 50 around the long axis of the stent 52, while the plurality of second undulations 30 may propagate helically 51. Note, the amplitude or height of the undulations forming the transition zone may be equal (see, 50 and 51). The stent may further comprise an end zone 53 which is formed from a cylindrical winding comprising a plurality of undulations. The end zone 53 may be attached to the transition zone 4 by at least one strut 55. The end zone 53 may further comprise at least one radiopaque marker 54. See, www.nitinol-europe.com/pdfs/stentdesign.pdf for a review of the design and makeup of radiopaque markers which are well known in the art. The radiopaque markers may assume a variety of different sizes and shapes. FIG. 8 shows one embodiment of a radiopaque marker 54 which contains a centrally placed marker hole 56.

Figure 9A:
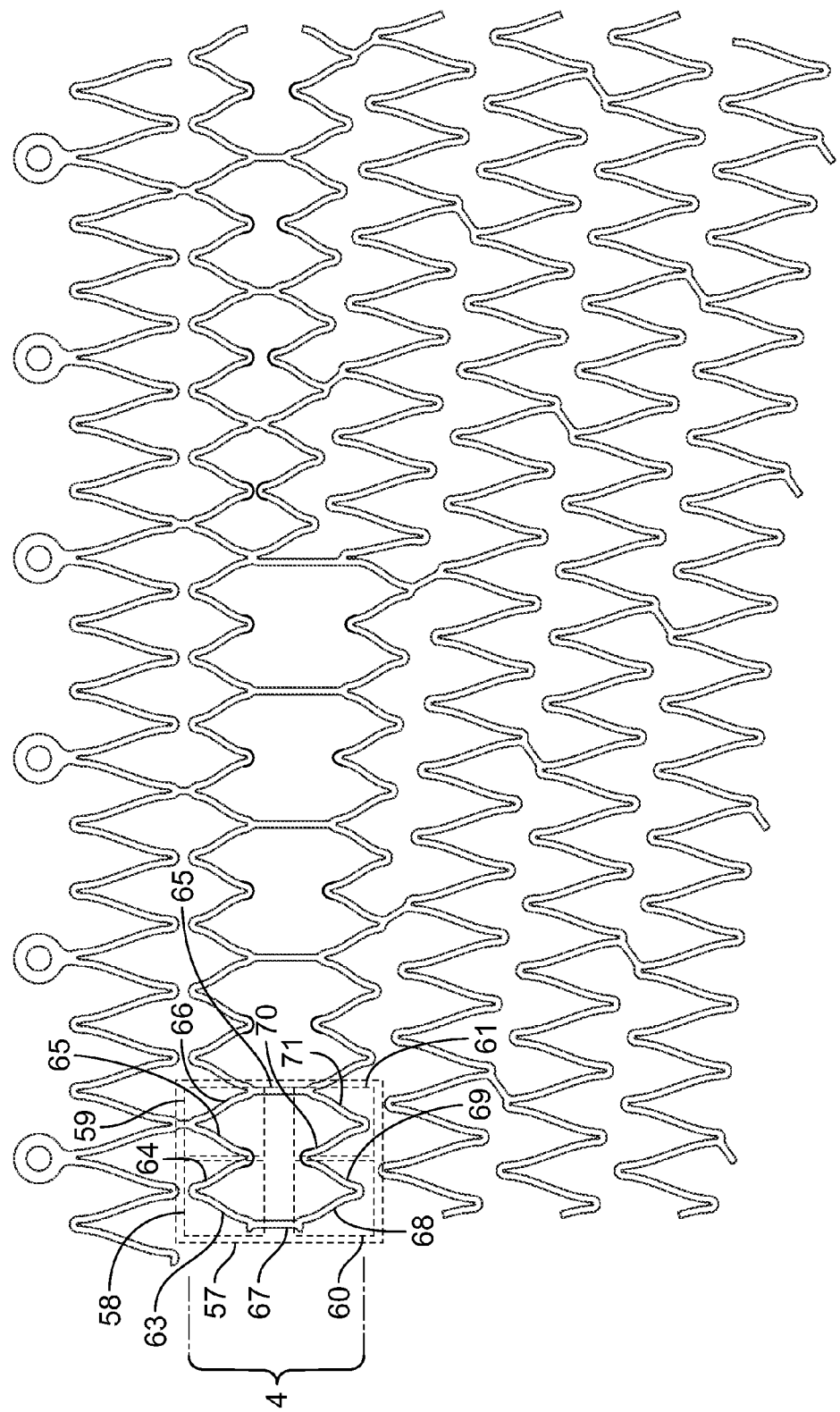
Figure 9B:
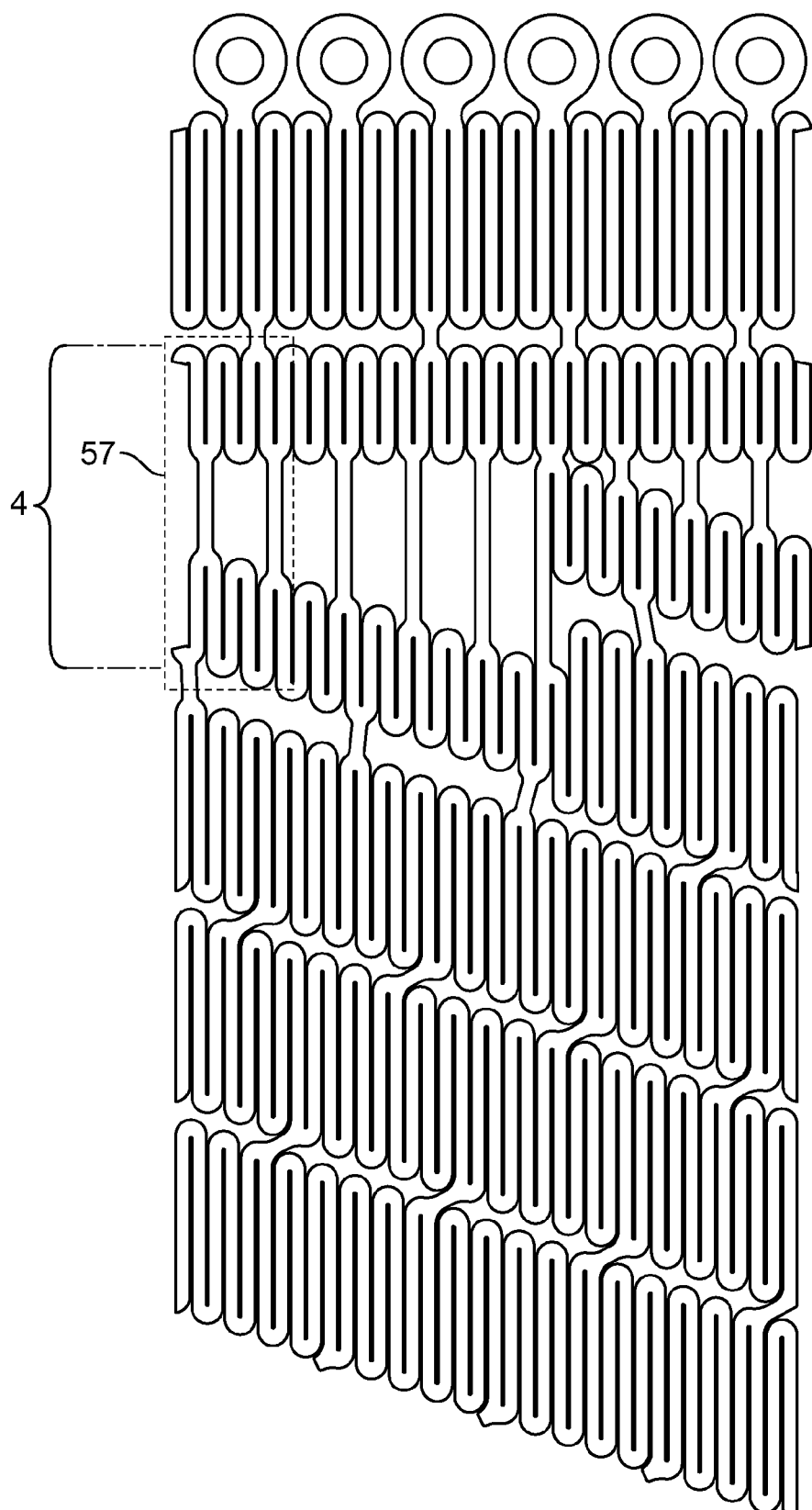

Although the polygons are shown as hexagons in the embodiments described in the figures, as discussed, the polygons can comprise an even number, such as, 4, 6, 8, 10, 12, 14, 16, 18, 20, 22, 24, 26, 28 and 30 sided polygons, up to an n-sided polygon. FIG. 9a presents an picture of one embodiment showing a 10-sided polygon in an expanded configuration. One 10-sided polygon of the transition zone 4 is labeled 57. FIG. 9b shows the sent of FIG. 9a in a crimped configuration. As is evident from the figures, the stent having a transition zone comprising a plurality of 10-sided polygons, behaves similarly to a stent having a transition zone comprising hexagons. The 10-sided polygon 57 comprises four undulations 58, 59, 60 and 61. Each undulation comprises two segments, undulation 58, segments 63,64, undulation 59, segments 65,66, undulation 60, segments 68,69 and undulation 61, segments 70, 71. The undulation 58 is connected by a segment 67 to undulation 60. Similarly, undulation 59 is connected to undulation 61 by a segment 65 to undulation 61. In the crimped configuration, opposite sides of the polygon are substantially parallel to one another, specifically refer to the following pairs, 63-64, 65-66, 68,-69 and 70-71 in the crimped configuration seen in FIG. 9b; also note, 61-65.

Figure 10A:
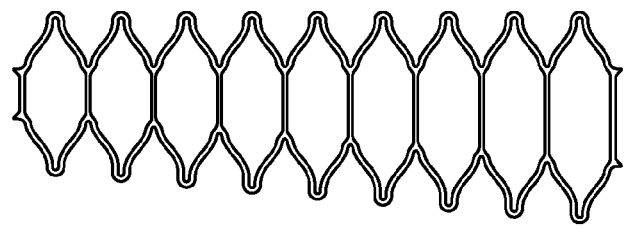
FIGS. 10a-10e—Various configurations of the polygons.
Figure 10B:
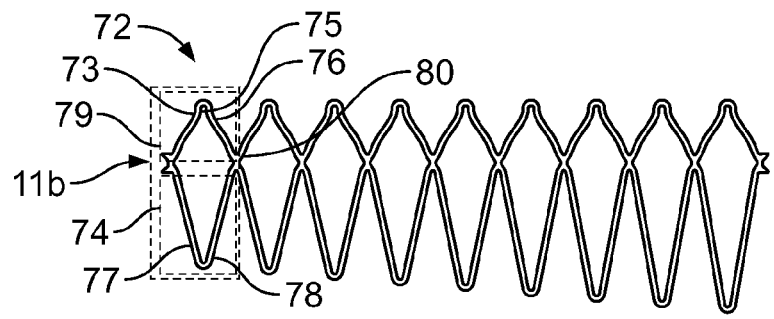
Figure 10C:
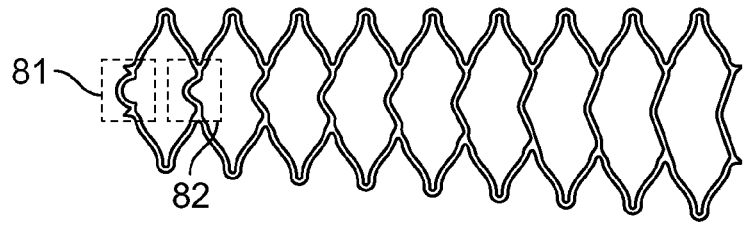
Figure 10D:
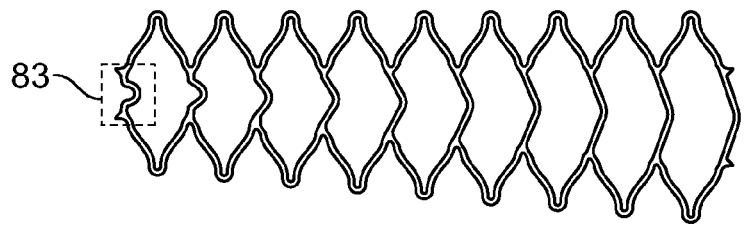
Figure 10E:
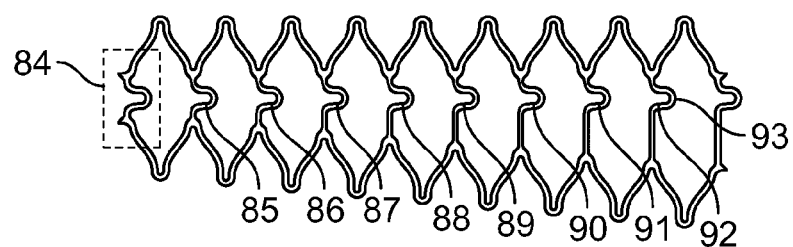

A wide variety of different configurations for the polygons as well as the various segments representing the sides of the polygon are encompassed by the present invention. In each of the various embodiments, the bending moment remains unchanged across the transition zone. FIGS. 10a-10e show various examples of these configurations. FIG. 10a shows the hexagonal configuration in FIG. 2 and is provided for comparison. In FIG. 10b, a polygon having segments with unequal length is shown. For illustration purposes only, one hexagon in the transition zone is labeled 72. The hexagon comprises two undulations 73 and 74, each having two segments 75,76 for undulation 73 and 77,78 for undulation 74. The two undulations 73,74 are connected by segments 79,80. The length of segments 77,78 is greater than the length of segments 75,76; the length of segments 77,78 are equal and the length of segments 75,76 are equal. This pattern, where the length of the segments comprising one undulation are greater than the length of the segments comprising the undulation making-up the segments of the opposing undulation, continues throughout the transition zone. FIG. 10c shows the polygons connected by a curvilinear segment 82 in one polygon; FIG. 10d shows the curvilinear segment running in the opposite direction. FIG. 10e shows the curvilinear portion 84-93 running throughout the transition zone.

The self-expanding stent of the present invention provides for a transition zone between the main body formed from a plurality of cylindrical winding of the stent and the end zone and where adjacent cylindrical windings are connected by at least one first strut. The transition zone is disposed at either end of the main body. The transition zone comprises a plurality of undulations where each undulation has two adjacent second struts connected by a loop. Although the width of the loop varies across the transition zone, the bending moment M of the loop remains constant across the transition zone allowing for uniform expansion. The specific bending moment M depends on the length, thickness and width of the struts and loops.

The stent may be inserted into the lumen of any vessel or body cavity expanding its cross-sectional lumen. The invention may be deployed in any artery, vein, duct or other vessel such as a ureter or urethra and may be used to treat narrowing or stenosis of any artery, including, the coronary, infrainguinal, aortoiliac, subclavian, mesenteric or renal arteries.

The dimensions of the stent may vary from about 10 mm to about 300 mm in length, from 20 mm to about 300 mm in length, from about 40 mm to about 300 mm in length, from about 20 mm to about 200 mm in length, from about 60 mm to about 150 mm in length, from about 80 mm to about 120 mm in length. In one embodiment, the stent may be about 88.9 mm. The internal diameter (I.D.) of the stent may range from about 2 mm to about 25 mm, from about 2 mm to about 5 mm (e.g., for the coronary arteries), from about 4 mm to about 8 mm (e.g., for neurological spaces in the CNS, both vascular and nonvascular), from about 6 mm to about 12 mm (e.g., for the iliofemoral), from about 10 mm to about 20 mm (e.g., for the ilioaortic) and from about 10 mm to about 25 mm (e.g., for the aortic).

Figure 11A:
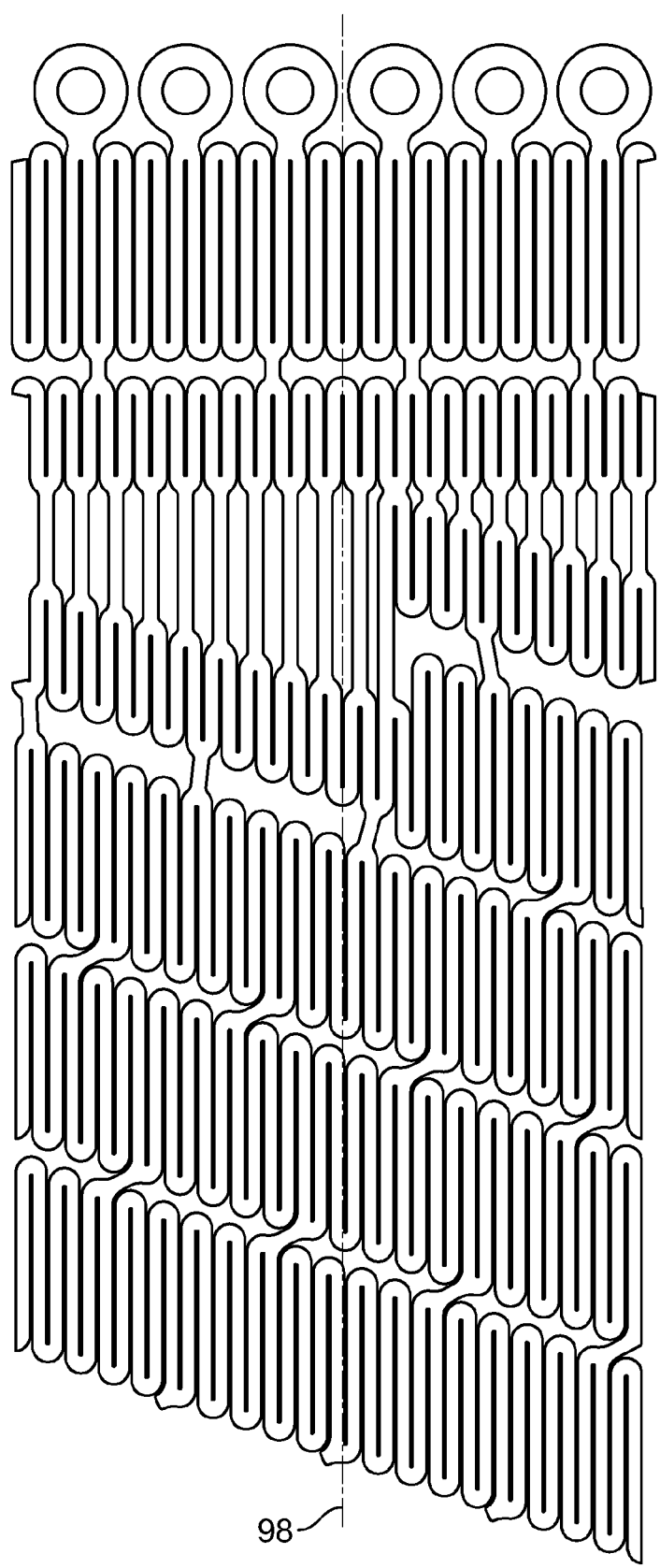

The main body 1 of the stent may be comprised a variety of different configurations. FIGS. 11a and 11b illustrates one embodiment of the stent in a crimped 11a and expanded 11b configuration. The main body 1 is composed of a plurality of cylindrical windings 2. The cylindrical windings 2 are themselves comprised of a plurality of undulations 94 (for clarity, only a single undulation in the cylindrical windings is illustrated with a number). The undulation 94 is comprised of two segments 95 and 96, which may be linear or curvilinear. The amplitude 100 of the undulation 99 may constant or vary across the main body 1 and may be equal to, less than or greater than the amplitude of the undulations of the transition zone 4. In the embodiment shown 100'<100. Adjacent cylindrical windings 2 are connected by a plurality of struts 3. In this embodiment, there are 5 segments between struts 3' and 3" (see, 97). However, there may be 2, 3 (e.g., U.S. Pat. No. 7,169,175), 4, 5 (e.g., U.S. Pat. No. 6,878,162), 6 (e.g., U.S. Pat. No. 6,551,351), 7 (e.g., U.S. Pat. No. 6,969,402), 8, 9 (e.g., U.S. Pat. No. 6,878,162), 10, 11, 12, 13 ,14, 15, 16, 17, 18, 19 or 20 segments between struts 3 to 3'; higher numbers of segments between struts are also possible with the design of the present invention. The width of the cylindrical windings may vary from about 0.05 mm to about 2.5 mm, from about 0.05 mm to about 1.3 mm, from about 1 mm to about 2 mm, from about 1.5 mm to about 2.5 mm. The thickness may vary from about 0.05 mm to about 0.3 mm, from about 0.1 mm to about 0.25 mm, from about 0.15 mm to about 0.20 mm and in one embodiment about 0.19 mm. The first struts 3 connecting adjacent cylindrical windings 2 may assume a wide variety of different angles relative to the main axis of the stent 98, including 0°-70°, 20°-60°, 30°-55° or 45°-50°. The angles may also be negative, i.e., fall on the opposite side of the long axis of the stent 98. The range of possible negative angles may be the same. The first struts 3 may all have the same or different angles with respect to the long axis of the stent 98. The dimensions of the struts 3 may vary and may be equal to the struts 10 connecting the main body to the transition zone 4.

The junction zone 99 between the main body 2 and the transition zone 4 can assume a variety of different configurations. In the embodiment shown in FIGS. 11b and 11c the amplitude 100 of the undulations 100 of the cylindrical windings 2 is greater than the amplitude 100' of the undulations of the transition zone 4; specifically, compare the lengths of segments 102 and 101. In addition, note that the amplitude 100 of the undulations in the cylindrical windings 1, 2 is greater than the amplitude 100' of the undulations on the transition zone 4. FIG. 11c shows an enlarged view of the junction zone 99; segment 100 of the undulation of the cylindrical windings 2 intersects a segment 103 of the transition zone 4 at a point approximately ⅓ along its length. Note, segment 103 connects two undulations. The segment 101 of the transition zone intersects the segment 103 of the transition zone 4. In addition, the length of segment 102 is greater than segment 101.

Figure 12A:
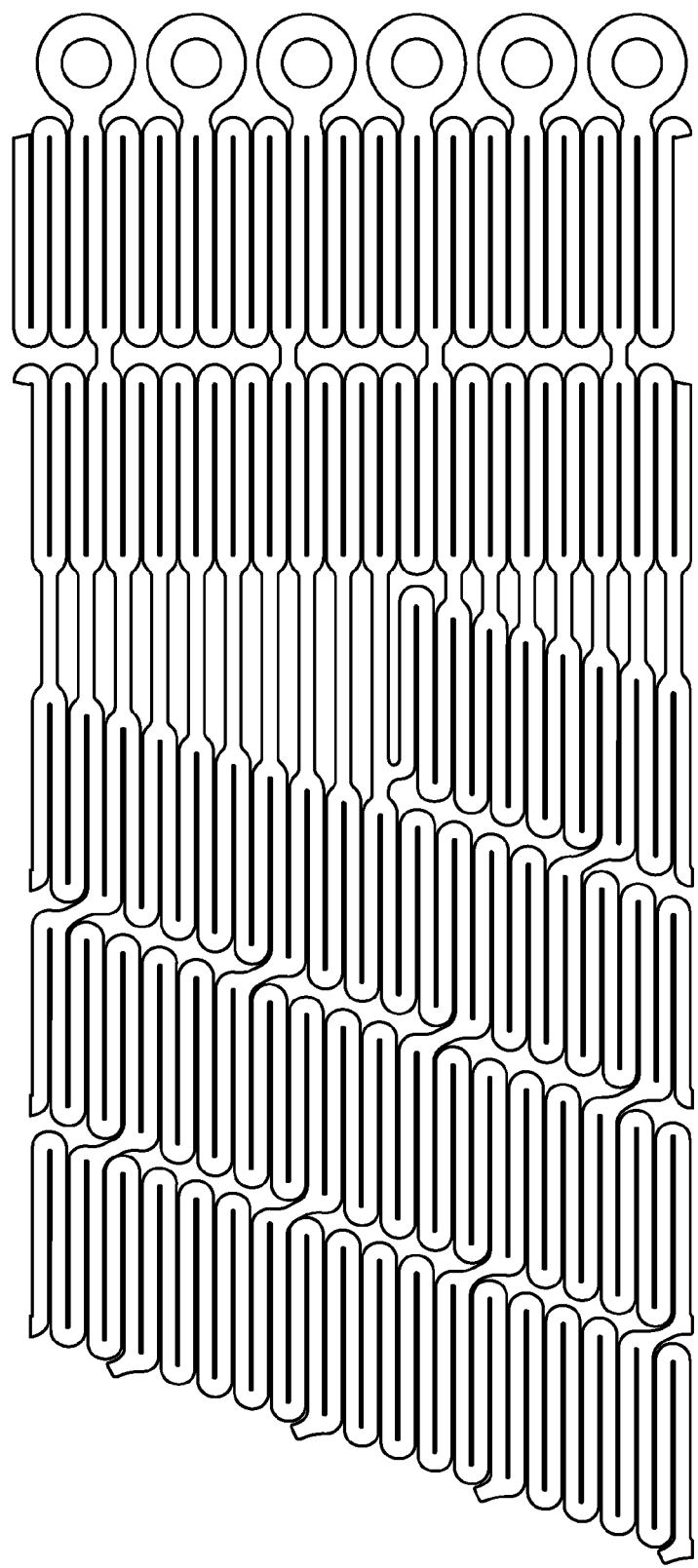
FIGS. 12a-c—Crimped and expanded views of one embodiment of the stent, including a close-up view of the junction zone.
Figure 12B:
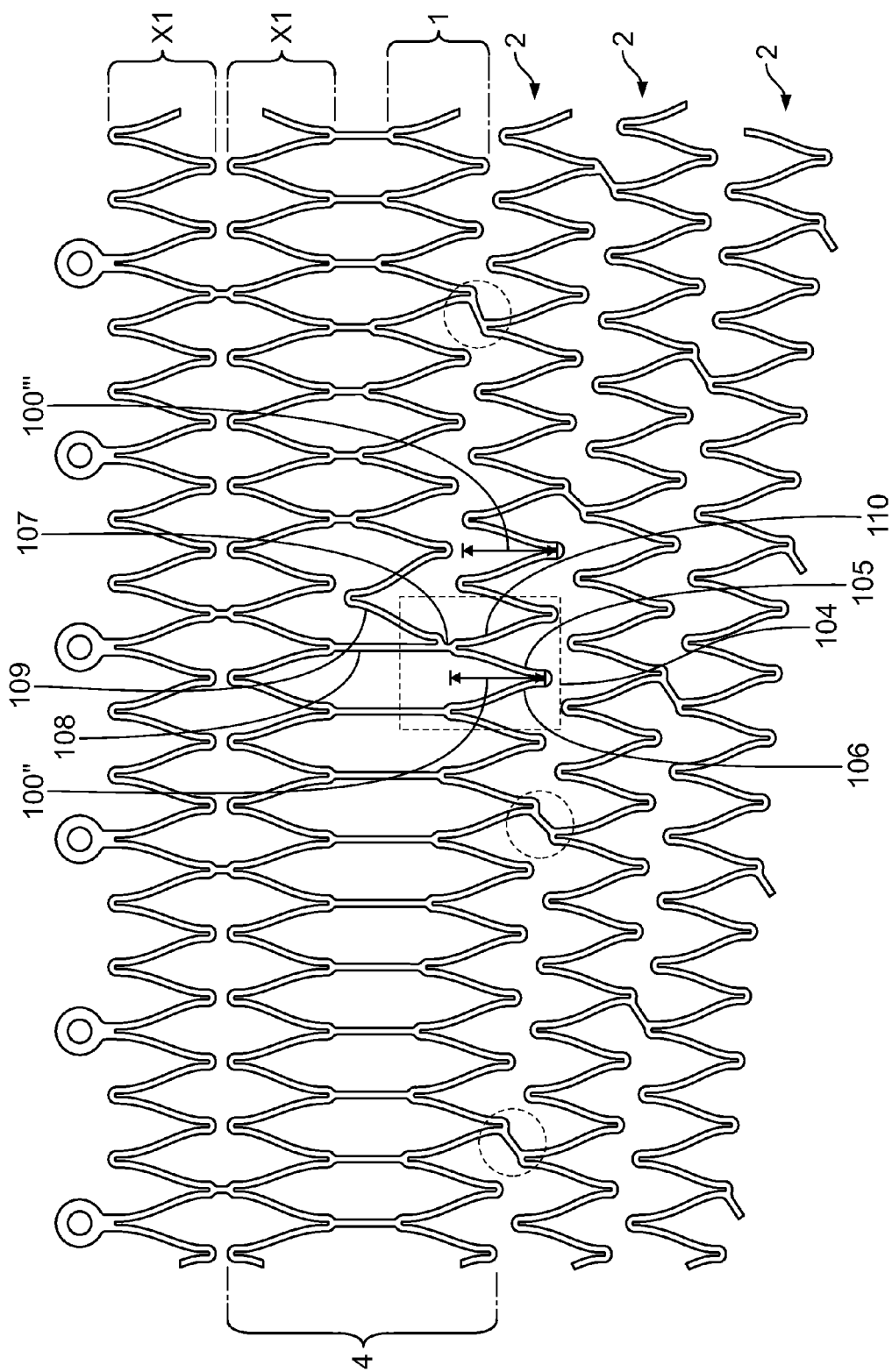
Figure 12C:
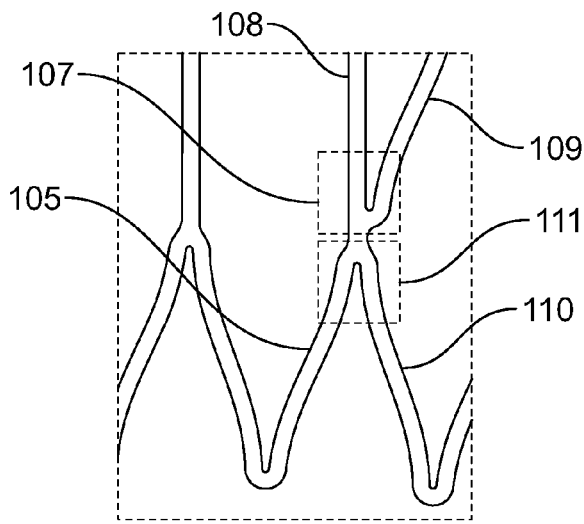
Figure 13A:
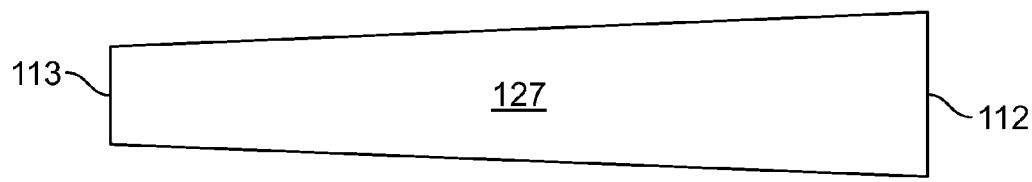
FIGS. 13a-d show various structural embodiments where the stent main body has a tapered design.
Figure 13B:
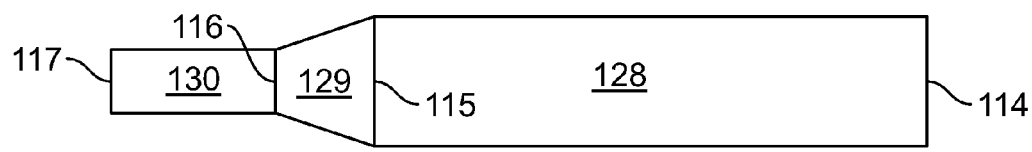
Figure 13C:
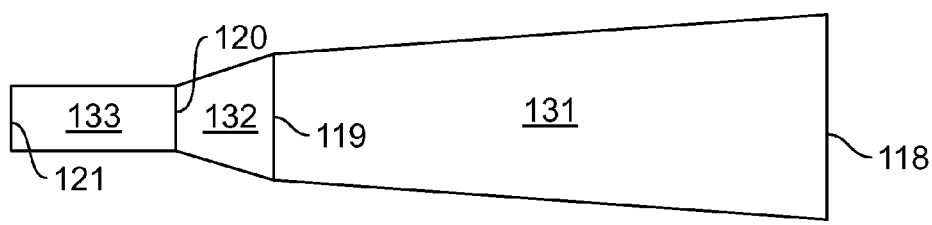
Figure 13D:
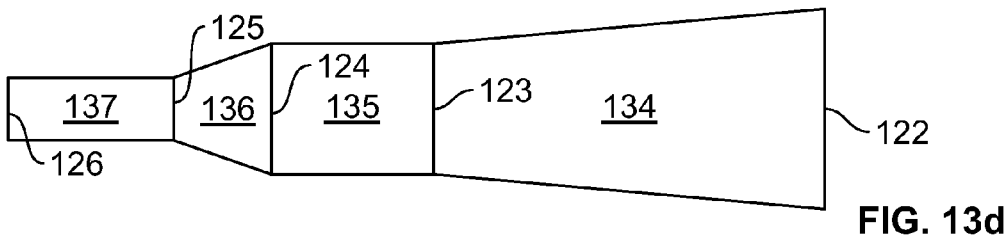

FIGS. 12a-c show another embodiment of the stent, where the length of the segments 110 of the cylindrical windings 2 are equal to the lengths of the segments 104, 105 of the undulations of the transition zone 4; in other words, the amplitude of the undulations in the main body 1 is equal to the amplitude of the undulations in the transition zone 4 (note 100" and 100'''). FIG. 13c shows an enlargement of the junction 104 of the cylindrical windings 2 and the transition zone 4. As is shown in the enlargement, segment 110 of the cylindrical windings 2 intersects the segment 105 of the transition zone 4. The segment 108 of the transition zone 4 which connects opposite undulations of the transition zone 4 forms a three-way junction 111 with segments 105 and 110. Segment 109 of the transition zone 4 forms another three-way junction 107 with segment 108 of the transition zone 4. Other embodiments of the juncture of the transition zone such as those found in U.S. Pat. Nos. 6,696,402 and 6,878,162 are encompassed by the present invention. For example, the junction can comprise a the trident which is comprised of two struts of a common hoop at the end of the transition zone, as well as an adjacent strut which is connected to either the beginning of the transition zone or the helical portion. The junction of the trident includes the hinge of the common hoop, as well as a hinge connecting the adjacent strut to the hinge of the common hoop. U.S. Pat. No. 6,969,402.

The main body 1 of the stent can assume a variety of different configurations. As shown in FIGS. 13a to 13d the main body of the stent can taper. For example, the diameter of one end of the stent 112 may be greater than the diameter of the other end of the stent 113 forming a tapered main body 127. The main body 1 may be formed from three sections 128, 129 and 130 where the ends of the sections 128 have equal diameters 114=115, section 129 comprises a tapered section where diameters 115 is greater than 116. Section 130 is uptapered with diameters 116=117. In another embodiment, section 131, diameter 118 is greater than 119, section 132, 119 is greater than 120, and in section 133, diameters 120=121. Another embodiment, shows two tapered sections 134 and 136 where diameters 122, 124 are greater than 123 and 125, respectively. Sections where no tapering is present 135 and 137 have constant diameters at either end, 123=124 and 125=126.

Figure 14:
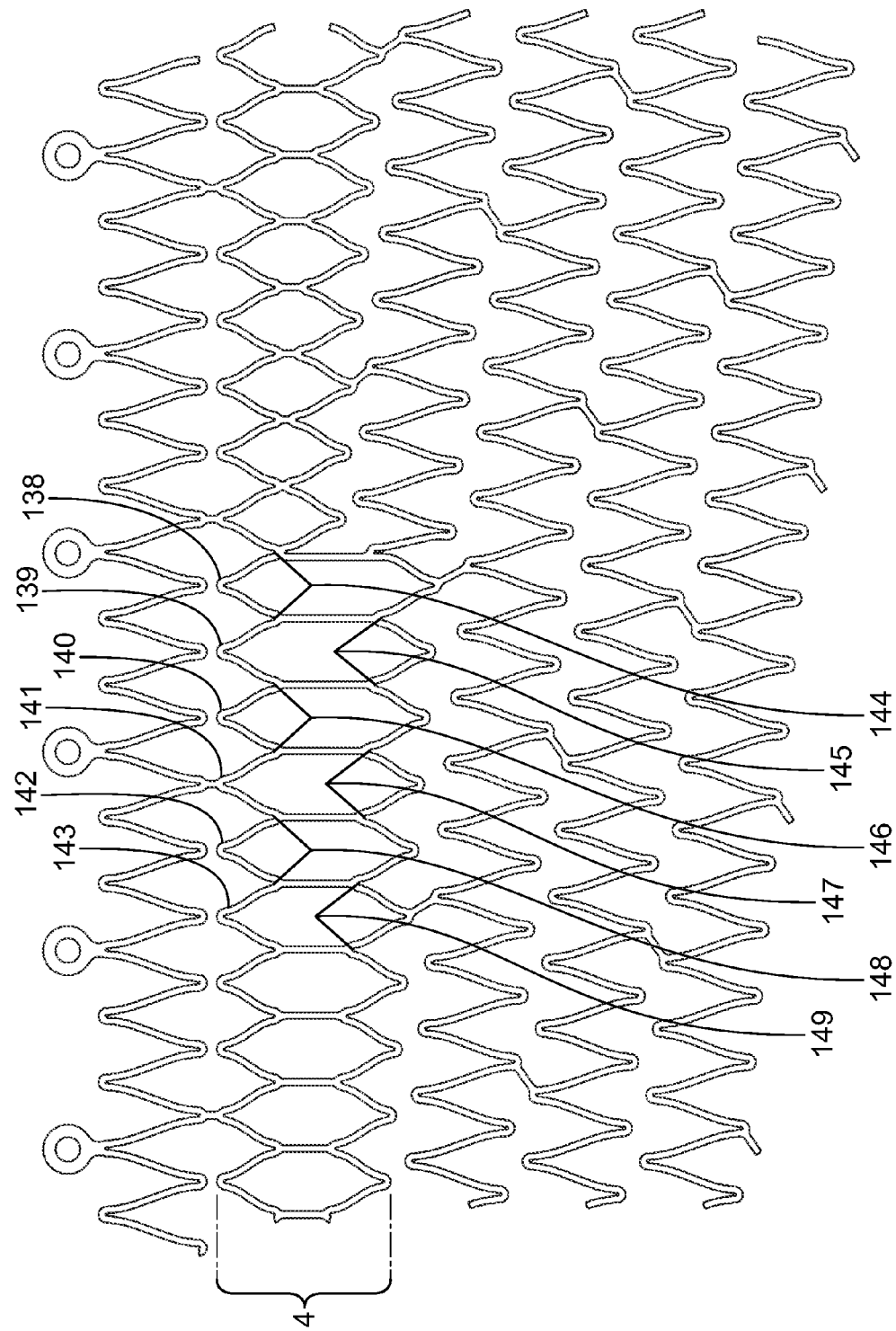
FIG. 14—A stent where the transition zone contains bridging elements.
Figure 15:
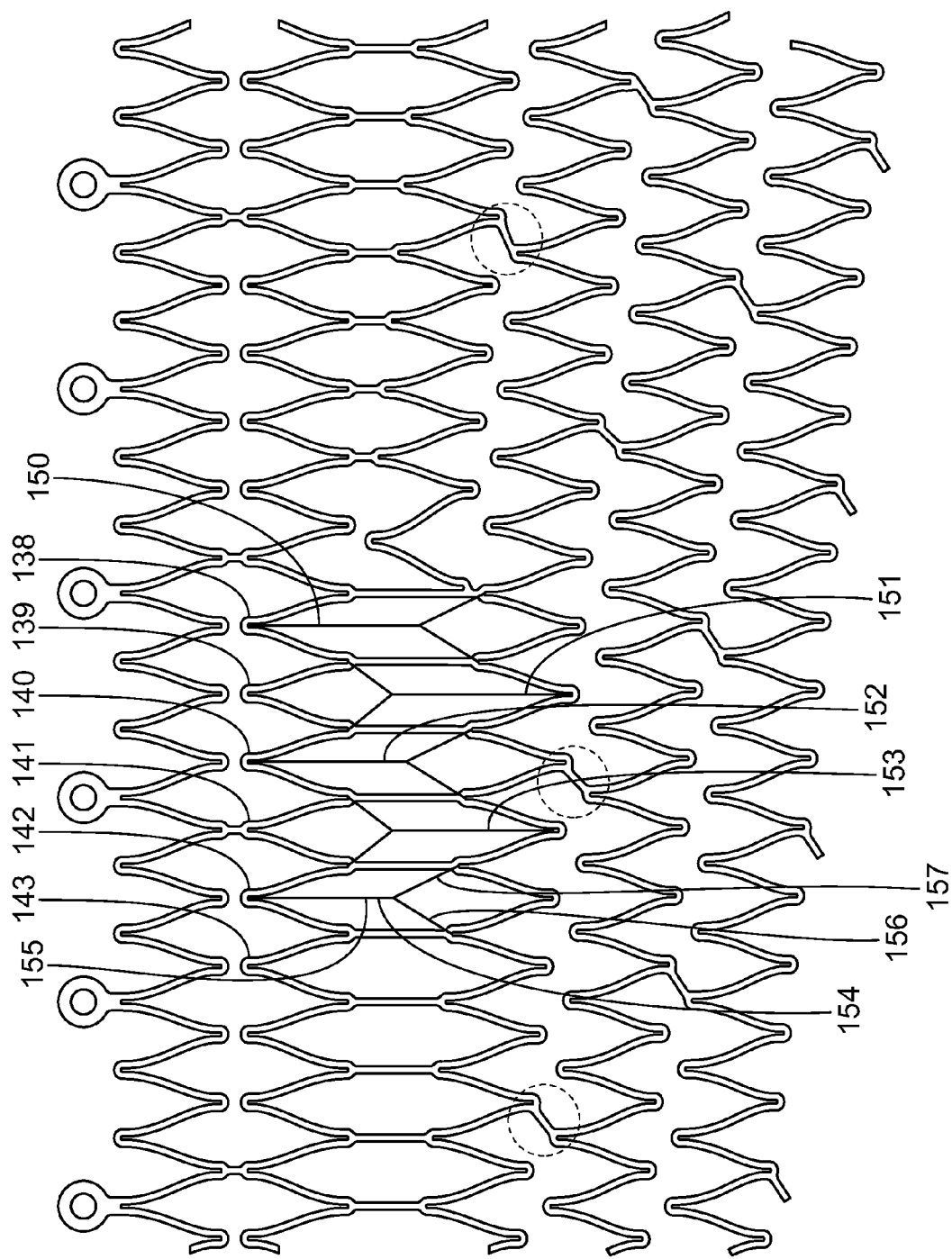
FIG. 15—Another embodiment of a stent containing bridging elements in the transition zone.

The polygons of the transition zone may be modified internally in various ways. For example, one embodiment of such a modification is shown in FIG. 14. As shown in the figure, the polygons of the transition zone 138-143 (note, not all of the polygons of the transition zone 4 are labeled), contain a bridging element 144-149. The bridging segments may comprise two segments which bridge or attach to the undulations forming the polygons (see, FIG. 14). The bridging elements may be formed from one or multiple segments which may linear or curvilinear. The bridging elements may be present in one, some or all of the polygons of the transition zone. For example, the bridging elements may be present in 1, 2, 3, 4, 5, 6, 7, 8, 9, 10, 11, 12, 13, 14, 15 or all of the polygons in the transition zone. FIG. 15 shows another embodiment of the bridging elements are composed of three segments 155, 156, 157. In this embodiment, the bridging elements are shown as a Y-shaped element; however, other shapes such as M, X, Y are also encompassed by the invention.

Figure 16A:
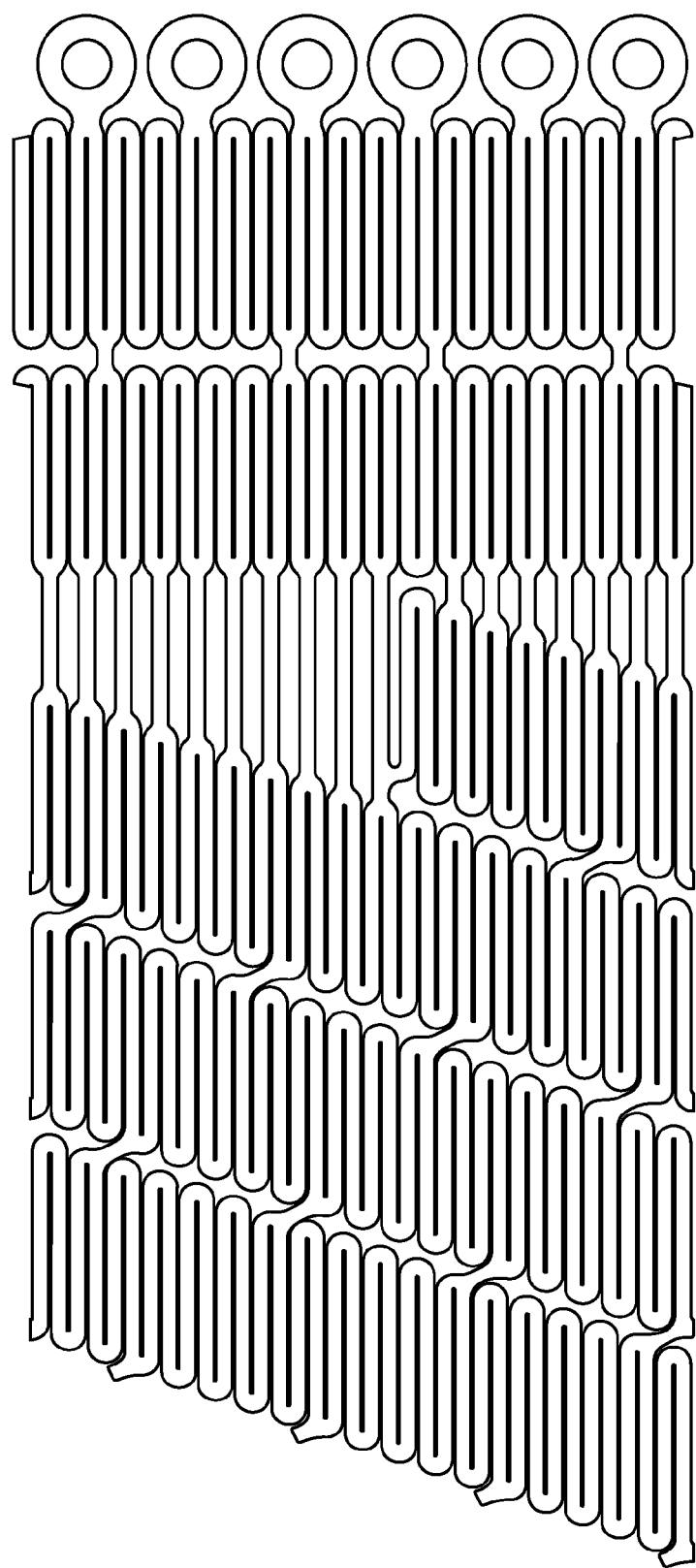
FIG. 16—A stent where the helical portion of the transition zone contains bridging elements.
Figure 16B:
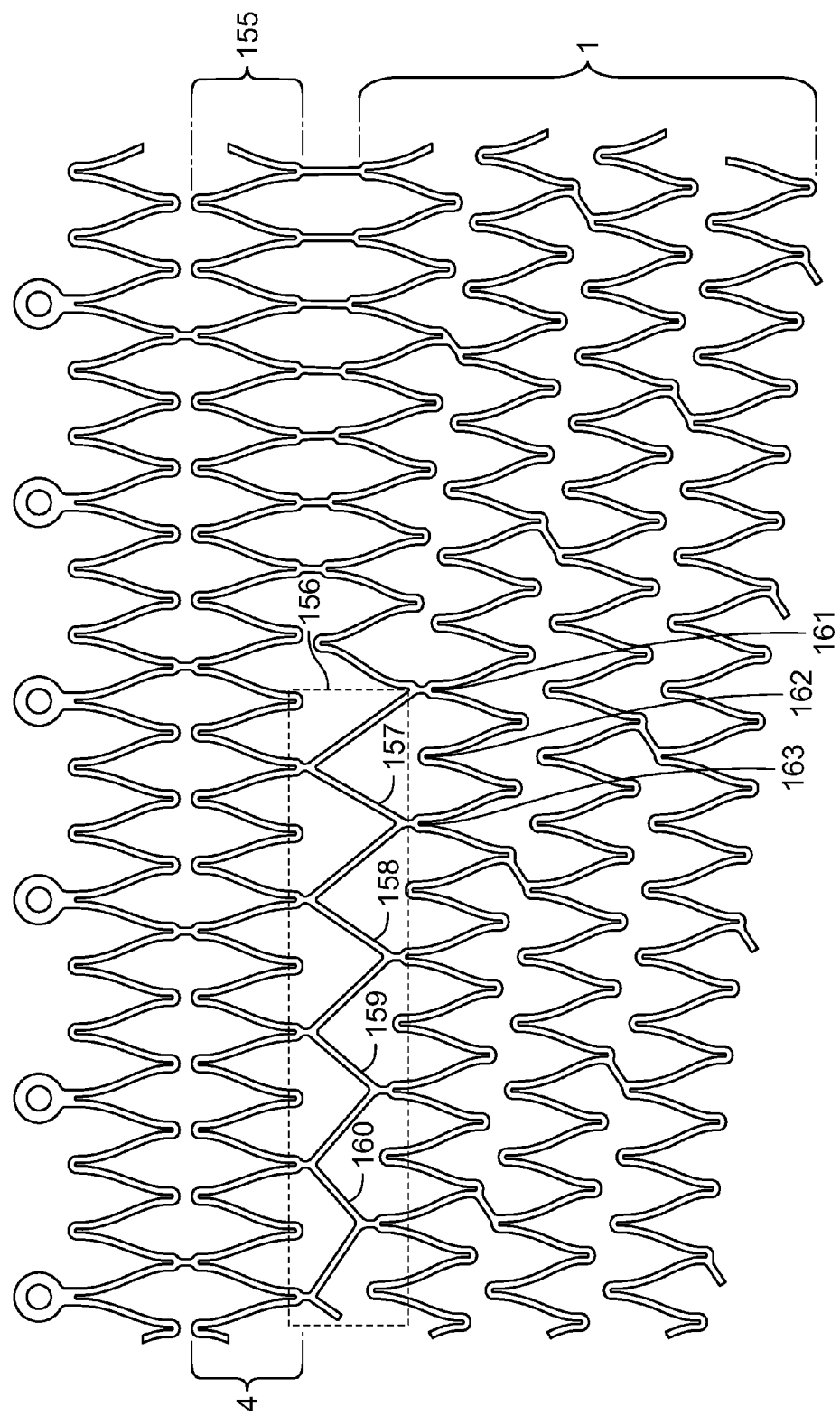

FIG. 16 shows another embodiment of the transition zone, where the helically propagating undulations 30,51, are replaced a set of meandering elements 157, 158, 159, 160, which are attached to every second 161, 163 undulation of the undulations of the main body 1. Other embodiments where a meandering element 157-160 is attached to every third, fourth, fifth, sixth, etc. undulation of the main body 1 are also possible within the scope of the invention (FIG. 16).

Figure 17:
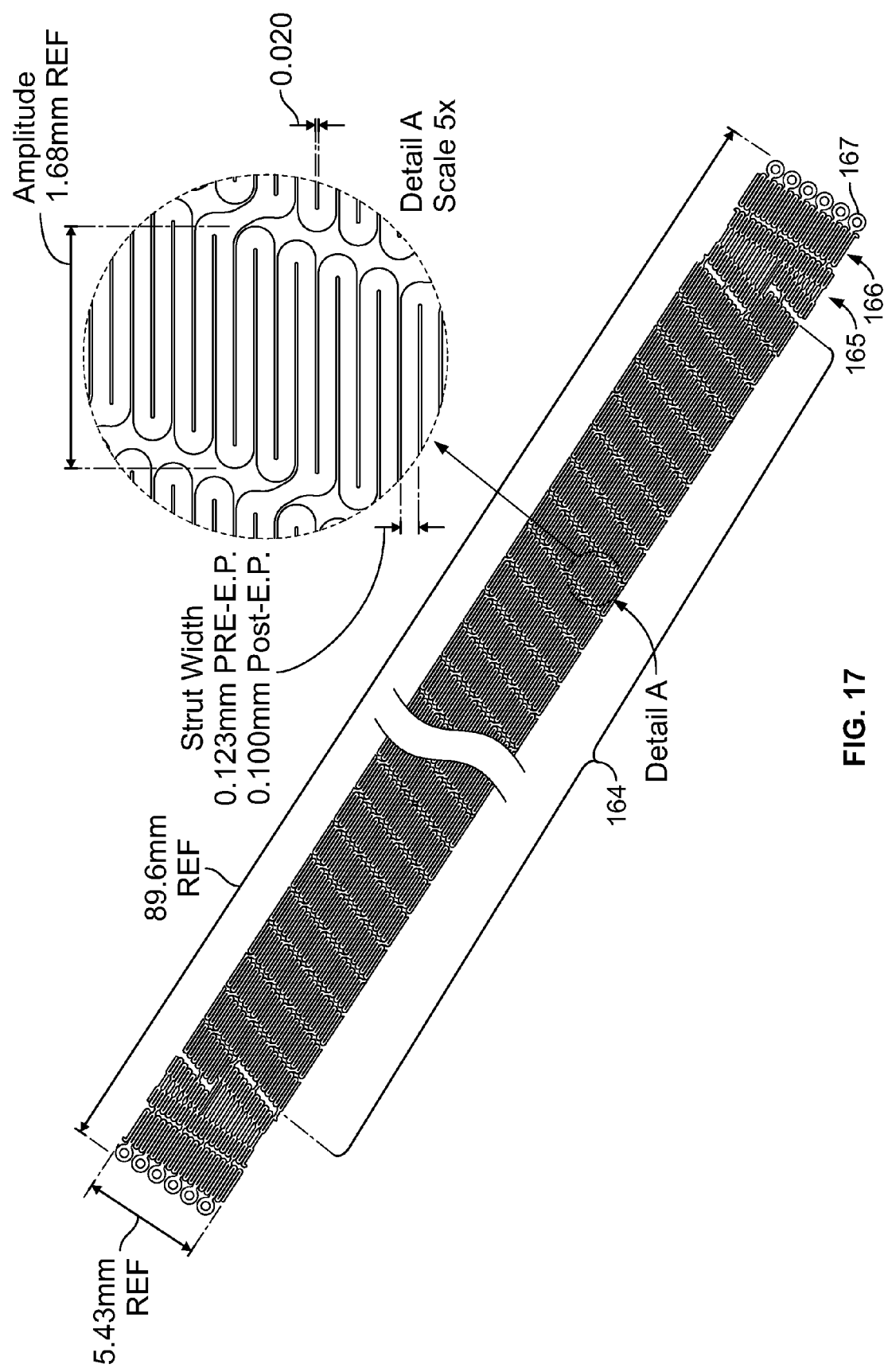
FIG. 17—Flattened overview of stent
FIG. 18a—Cut view of stent with close-up of transition zone
FIG. 18b—Close-up of undulation with a hole
FIG. 18c—Close-up of hole and loop width
FIG. 19—Transition zone
FIG. 20—Bending Moment with undulation
FIG. 21a—Expanded, flattened view of stent
FIG. 21b—FEA results of transition zone
FIG. 22—Alternative embodiments of undulations in transition zone
FIG. 23—Cylindrical windings
FIG. 24—Flattened view of expanded stent with juncture and transition zone
FIG. 25—Various embodiments of main body
Figure 18A:
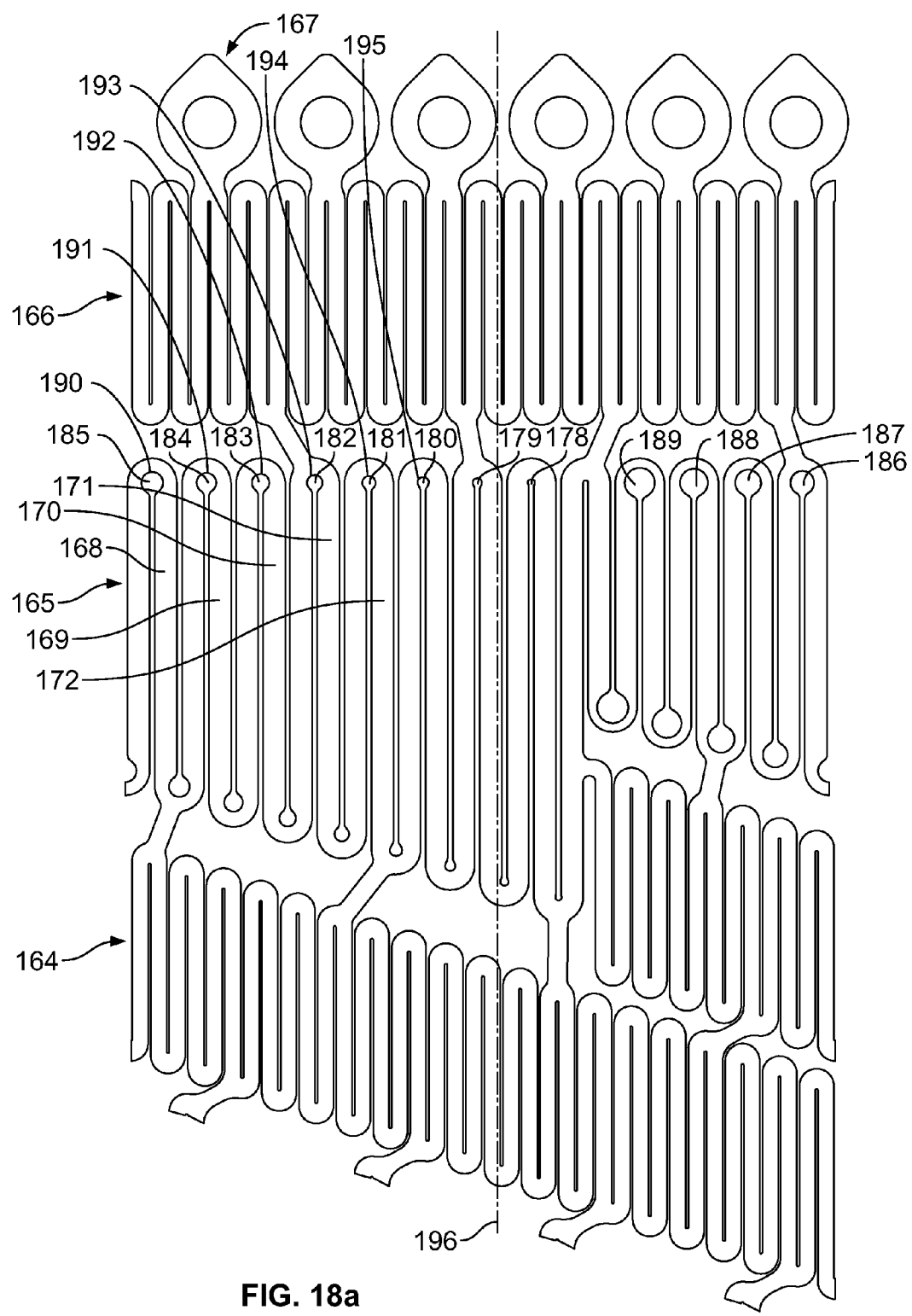
Figure 18B:
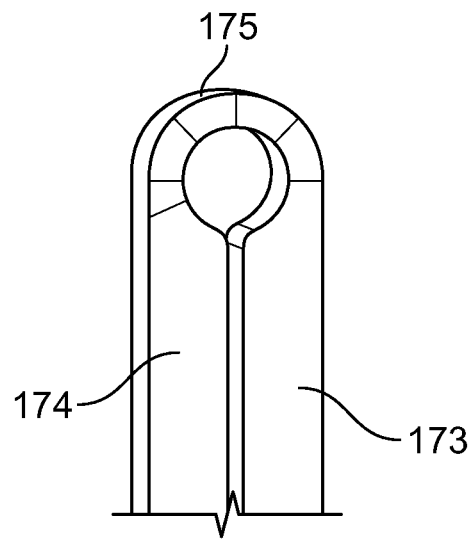

The stent pattern may also be formed with a transition zone comprising struts of varying length and thickness. FIGS. 17 and 18 show flat images of one embodiment of the stent in a crimped, FIG. 17, and expanded, FIG. 18, state. The main body of the stent 164 is connected to the transition zone 165. The transition zone may be capped with an end zone 166 which may have attached a plurality of radiopaque markers 167. FIG. 18a shows a cut, flat image of the stent in FIG. 17 that more closely illustrates the transition zone 165. The transition zone comprises a plurality of undulations (for clarity, only a selected number of illustrations, 168-172 are labeled in FIG. 18a). The undulations are formed from two adjacent second struts, 173, 174 (again only one such undulation is shown in FIG. 18b, however, all undulations have a similar structure). The second struts are connected by a loop, 175. The width of the loop 176 varies across the transition zone 165.

A hole or space 177 may be present in a portion of the loop 176. The hole 177 may be semicircular, but may also assume other shapes, such as a semicircular hole with an extrusion or dimple positioned at one portion of the circumference. The area of the hole may be calculated using standard mathematical formulas for determining area (http://www.engineersedge.com/area_properties/area_calc_menu.shtml, June, 1009).

Figure 18C:
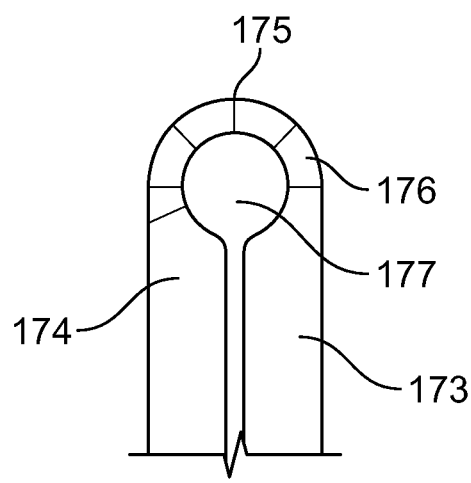

The width 176 of the loop 175 may be measured from the edge of the space or hole 177 to the outer edge of the loop 176. FIG. 18c. The hole 177 is formed from an adjacent pair of second struts 173, 174 and the loop 176. As is evident from FIG. 18a, the surface area of the hole 177 can increase either clockwise or counterclockwise relative to the long axis of the stent 196 (see, 178-189). The change in the surface area of the hole 177 correlates inversely with the width 176, i.e., as the surface area increases the width decreases (compare, surface areas 180-190 with widths 190-195).

Figure 19:
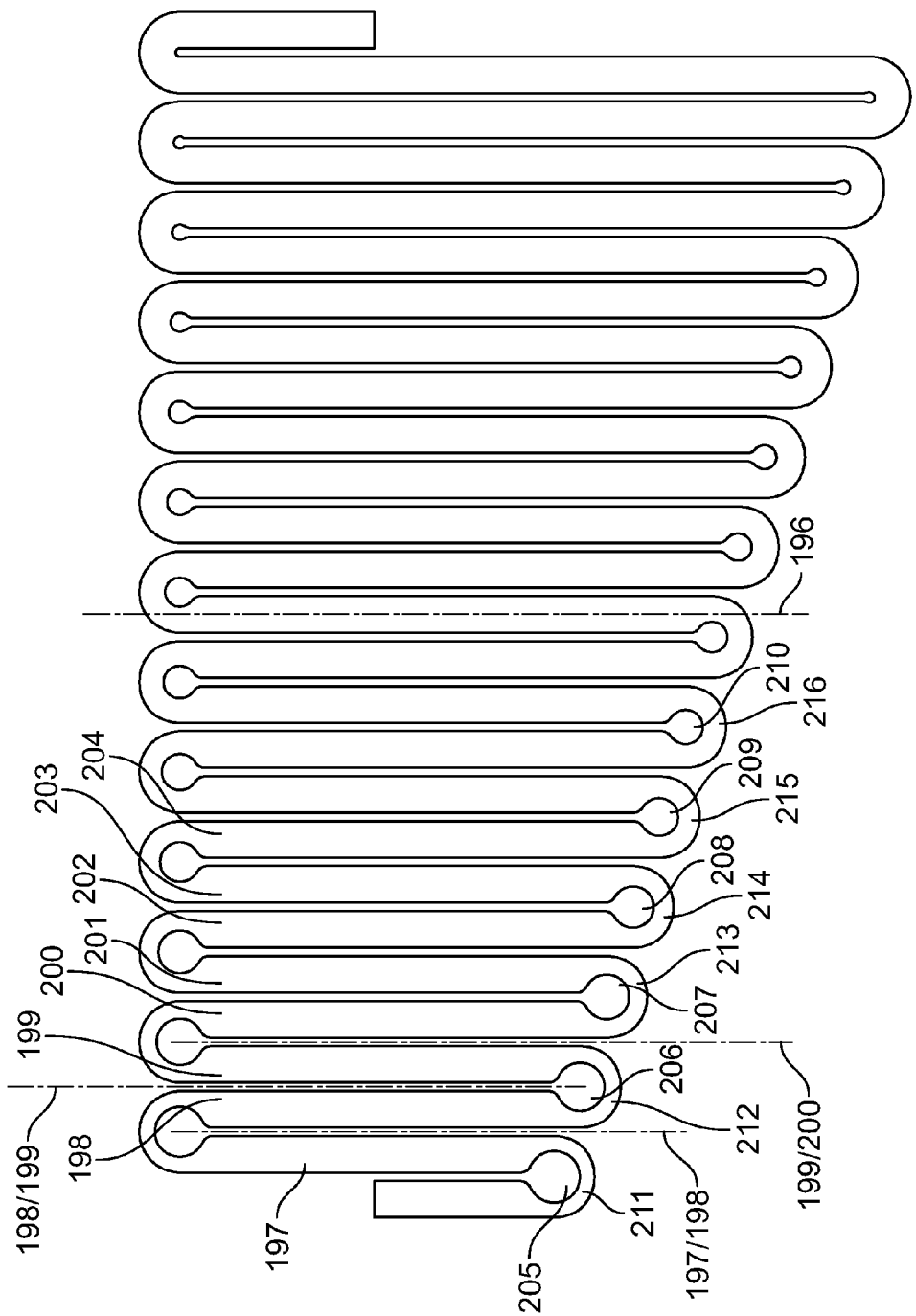

The second strut length changes across the transition zone 165. In FIG. 19, the second strut length increase clockwise around the long axis of the stent 196. This is illustrated by noting second struts 197-204. The surface area of the hole 177 decreases as the length of the second struts increases. Specifically, note 197-204 as compared with 205-210; in contrast, the width of the loop increases, note 211-216. Note the changes, length, surface area or width can vary clockwise or counterclockwise relative to the long axis of the stent. The variation of surface area, length and strut length across the transition zone 165 can be linear, geometric or assume some other nonlinear increase or decrease. The second struts may be straight or curvilinear. The curvilinear second struts may be concave and convex with curvature present at selected portions of the second struts. The degree of curvature may vary.

The length of the space lying between two second struts also varies across the transition zone 165. Specifically, the length of the space—shown as 197/198, 198/199 and 199/200, increases across the transition zone 165 as the length of the second strut increases. In other words, the length of the space is not constant or approximately constant, but varies, in a continuous or discontinuous fashion.

Figure 20:
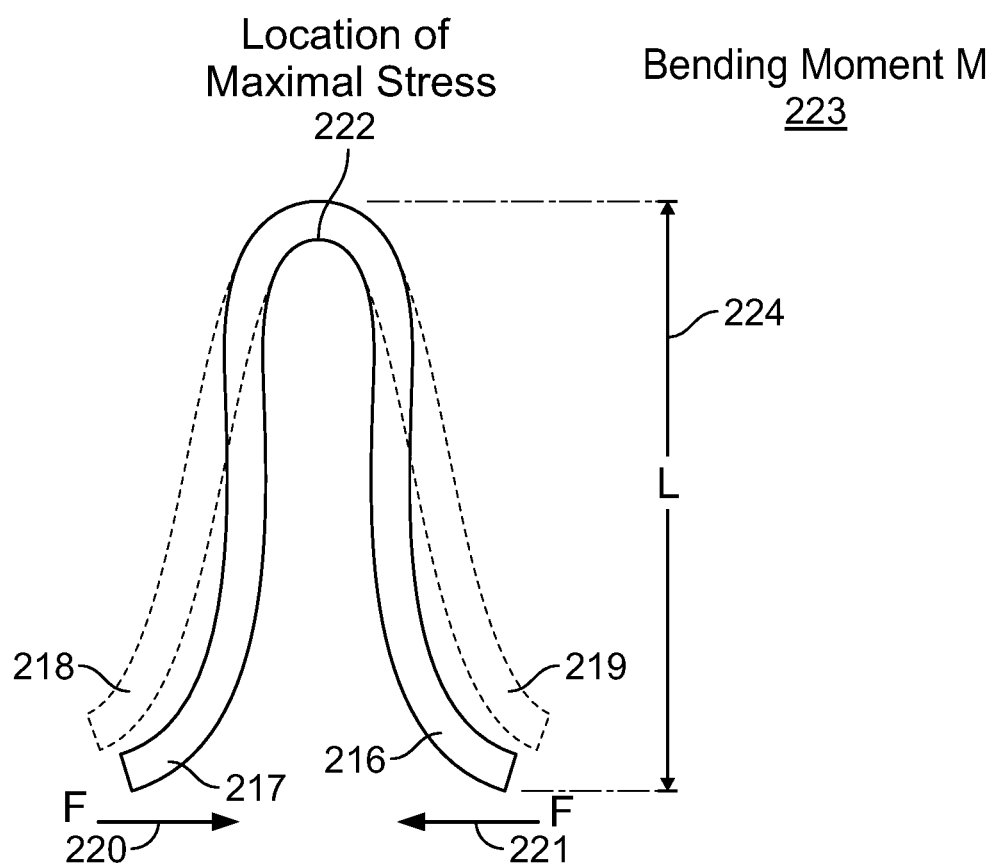

When the segments 218,219 are crimped (shown diagrammatically by the application of force, F (220,221) and 216,217), the bending moment, M 223, is measured at 222. The bending moment M 223 is calculated as: $M=F(L+r_n)$, where F, 220,221, is the force applied, L is the length of the segments 218, 219, and $r_n$ is the neutral radius where there is zero stress or strain along the curved or bent portion. See, http://www.roymech.co.uk/Useful_Tables/Beams/Curved_beams.html (April, 2009), http://courses.washingion.edu/mengr354/jenkins/notes354.html (April, 2009) for calculations of stress, strain and bending moments in curved beams (see, FIG. 20).

Figure 21A:
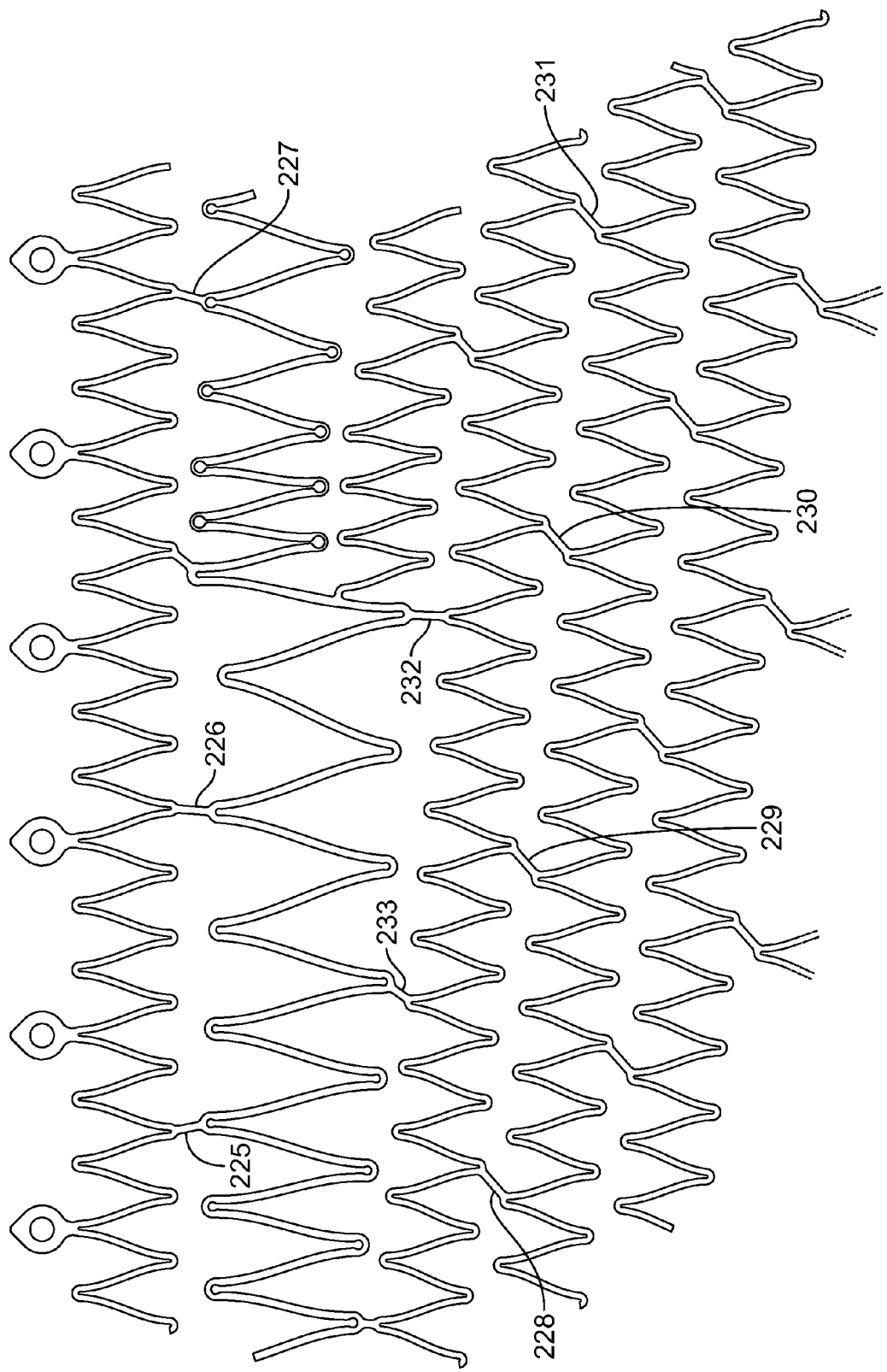

Another embodiment of the stent in an expanded configuration is shown in FIG. 21a. Note, the cylindrical windings of the main body are connected to each other by a plurality of first struts, 228-233, and to the transition zone. The number of first struts in each helical turn may vary (see below for discussion of other embodiments). The first struts may assume a variety of angles relative to the long axis of the stent, including, 0-20°, 20-40° and 40-60° (the angle of these struts may be positive or negative relative to the long axis of the stent). The first struts may have the same or different angles with respect to one another. The width and thickness of the cylindrical windings varies, but may be equal to the width and thickness of the second struts. For example, the width of the cylindrical windings may vary from about 0.05 mm to about 0.2 mm, from about 0.075 mm to about 0.15 mm, from about 0.1 mm to about 0.130 mm and in one embodiment about 0.123 mm after electropolishing. The thickness may vary from about 0.05 mm to about 0.3 mm, from about 0.1 mm to about 0.25 mm, from about 0.15 mm to about 0.20 mm and in one embodiment about 0.19 mm. The transition zone 165 is connected to the end zone 166 by a plurality of third struts 225-227.

Figure 21B:
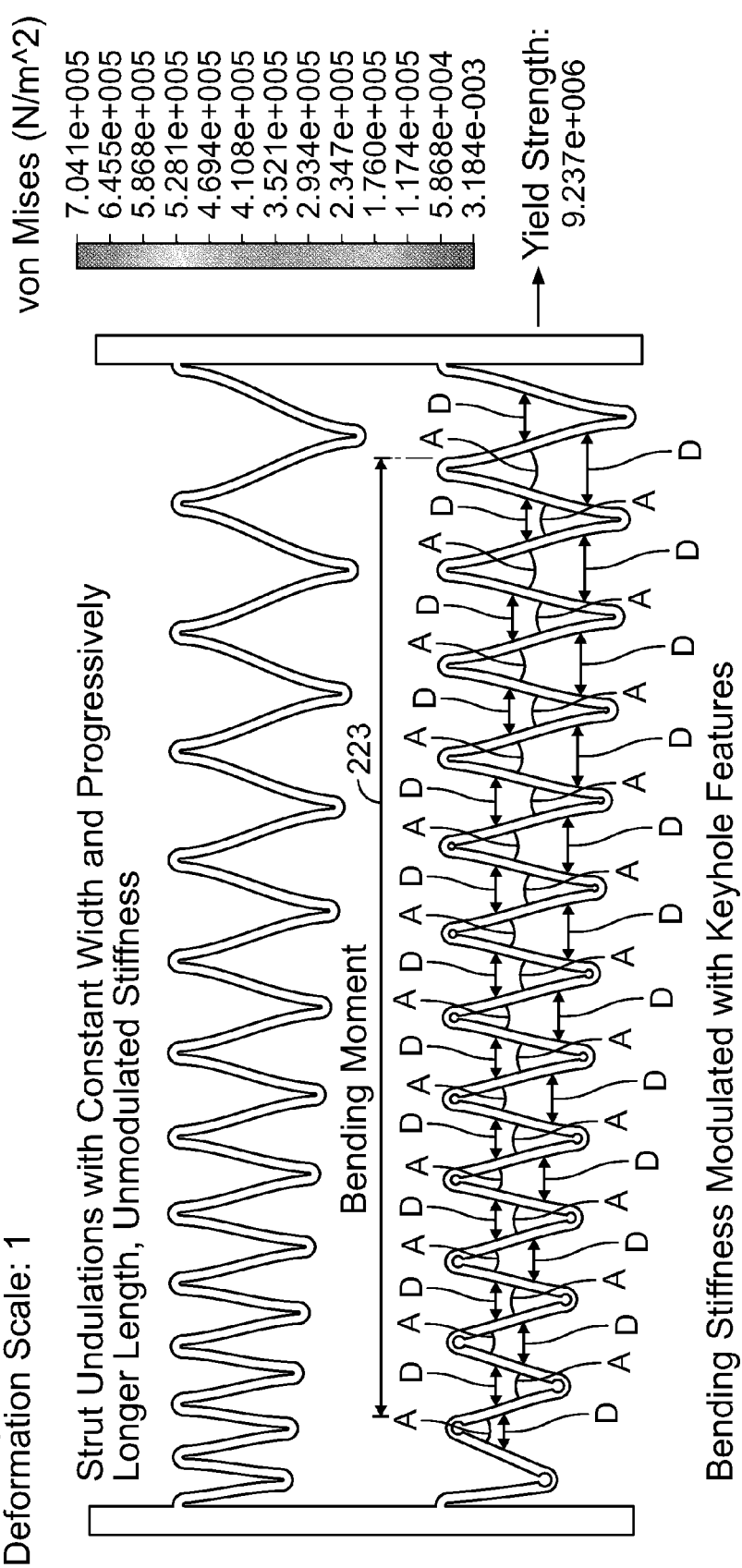

Empirically, the bending moment M 223 may be measured by finite element analysis, (FEA). Application of FEA analysis to stents is well known in the art and provides both a numerical and visual representation of stress and strain across the body of the stent. http://www.stent-ibitech.u-gentbe/research/fea.htm, April 2009. Software for FEA analysis is commercially available (http://www.mscsoftware.com/success/details.cfm?Q=286&sid=352, April, 2009). The following FEA analysis shows that the bending moment M 223 of each undulation in the transition zone remains constant across the transition zone 165, FIG. 21b. Thus, the geometry of the stent design allows for a constant bending moment, opening distance D and opening angle A across the transition zone as the stent expands. FIG. 21b.

A wide variety of different configurations of the undulations and holes are possible in the transition zone 165 (FIG. 22). Several possible designs are illustrated in FIG. 22. For example, the undulations may comprise an arch where there is a shoulder 238,239 and a loop 240. The width of the loop 240 increases across the transition zone 234-237. The transition zone can also comprise a plurality of flattened loops 241-244, where the width of the flattened loops increases across the transition zone 241-248. The shapes of the holes may vary as shown by FIG. 22 where the holes 253-259 form a dimple in one portion of the hole 260. Other configurations are also encompassed by the invention.

Figure 23:
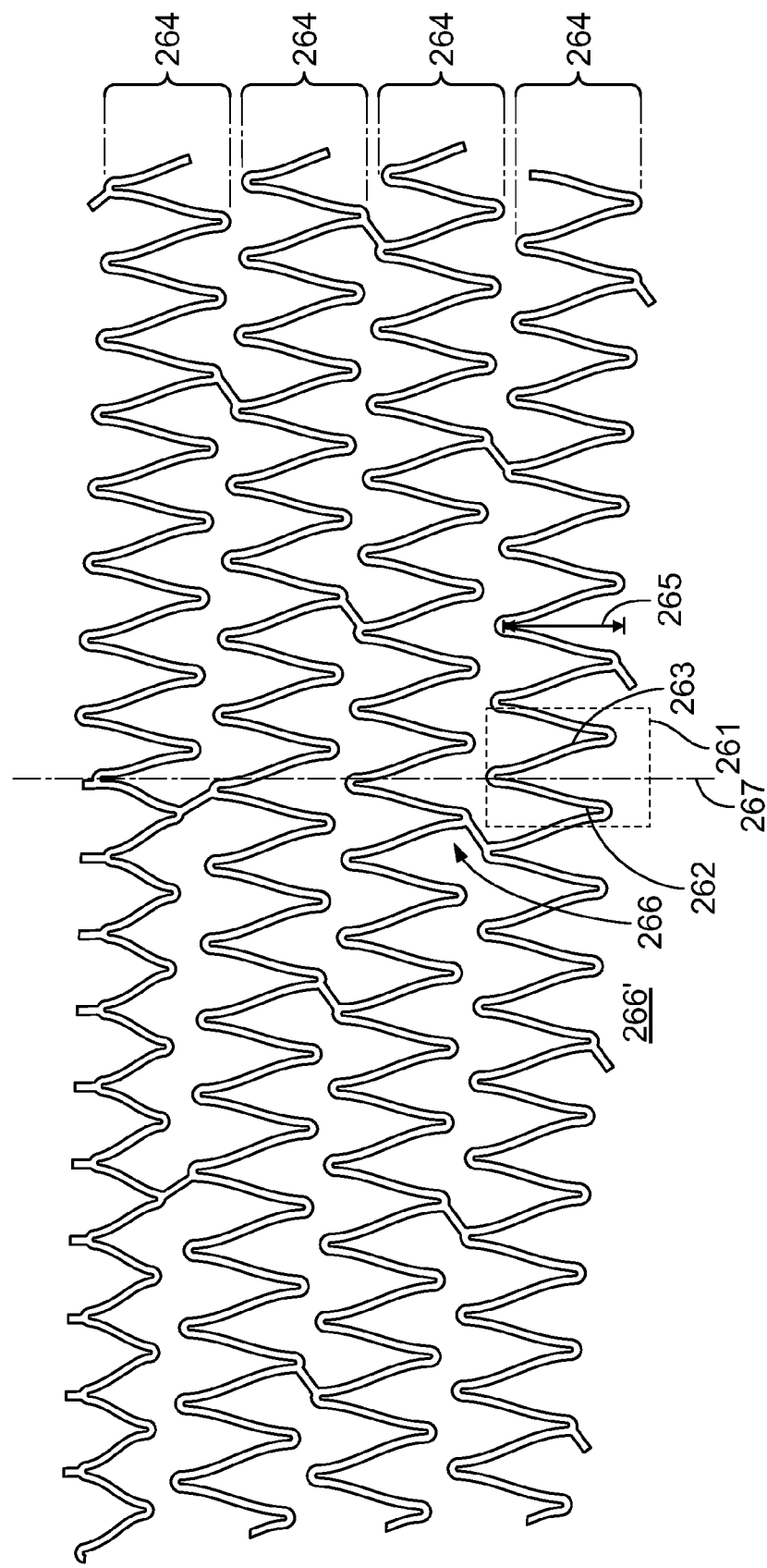

The main body of the stent 164 may comprise a cylindrical winding 264 which comprises a plurality of second undulations 261 (for clarity, only a single undulation is highlighted in FIG. 23). The second undulation 261 is comprised of two segments. The segments may be linear or curvilinear and may have bends positioned along their length. The segments may be equal or unequal in length. The length of these segments may vary from about 0.5 mm to about 3 mm, from about 1.0 mm to about 2.5 mm, from about 1.5 mm to about 2.0 mm and in one embodiment about 1.68 mm. The cylindrical winding 264 may propagate helically, U.S. Pat. No. 7,169,175 or may comprise a series of circumferential elements as described in U.S. Pat. No. 7,329,277. The second undulations in adjacent helical turns may be connected by at least one first strut. Note, the amplitude or height of the undulations forming the transition zone may be equal to that of the amplitude and height of the undulations comprising the cylindrical windings.

The amplitude 265 of the undulation 261 may be constant or vary across the main body 164 and may be equal to, less than or greater than the amplitude of the undulations of the transition zone 165. Adjacent cylindrical windings 264 are connected by a plurality of first struts 263. In this embodiment, there are 5 segments between first struts 266 and 266' (see, 263). However, there may be 2, 3 (e.g., U.S. Pat. No. 7,169,175), 4, 5 (e.g., U.S. Pat. No. 6,878,162), 6 (e.g., U.S. Pat. No. 6,551,351), 7 (e.g., U.S. Pat. No. 6,969,402), 8, 9 (e.g., U.S. Pat. No. 6,878,162), 10, 11, 12, 13 ,14, 15, 16, 17, 18, 19 or 20 segments between first struts 266 to 266'; higher numbers of segments between first struts are also possible with the design of the present invention. The width of the cylindrical windings may vary from about 0.05 mm to about 2.5 mm, from about 0.05 mm to about 1.3 mm, from about 1 mm to about 2 mm, from about 1.5 mm to about 2.5 mm. The thickness may vary from about 0.05 mm to about 0.3 mm, from about 0.1 mm to about 0.25 mm, from about 0.15 mm to about 0.20 mm and in one embodiment about 0.19 mm. The first struts 266, 266' connecting adjacent cylindrical windings 264 may assume a wide variety of different angles relative to the long axis of the stent 267, including 0°-70°, 20°-60°, 30°-55° or 45°-50°. The angles may also be negative, i.e., fall on the opposite side of the main axis of the stent 267. The range of possible negative angles may be the same. The first struts 266, 266' may all have the same or different angles with respect to the long axis of the stent 267. The dimensions of the first struts 266, 266' may vary.

The stent may further comprise an end zone 166 which is formed from a cylindrical winding comprising a plurality of undulations. The end zone 166 may be attached to the transition zone 165 by at least one third strut 225, 226, 227. The end zone 166 may further comprise at least one radiopaque marker 167. See, www.nitinol-europe.com/pdfs/stentdesign.pdf for a review of the design and makeup of radiopaque markers which are well in the art. The radiopaque markers may assume a variety of different sizes and shapes. The radiopaque marker may be centrally placed.

The dimensions of the stent may vary from about 10 mm to about 300 mm in length, from 20 mm to about 300 mm in length, from about 40 mm to about 300 mm in length, from about 20 mm to about 200 mm in length, from about 60 mm to about 150 mm in length, from about 80 mm to about 120 mm in length. In one embodiment, the stent may be about 88.9 mm. The internal diameter (I.D.) of the stent may range from about 2 mm to about 25 mm, from about 2 mm to about 5 mm (e.g., for the coronary arteries), from about 4 mm to about 8 mm (e.g., for neurological spaces in the CNS, both vascular and nonvascular), from about 6 mm to about 12 mm (e.g., for the iliofemoral), from about 10 mm to about 20 mm (e.g., for the ilioaortic) and from about 10 mm to about 25 mm (e.g., for the aortic).

Figure 24:
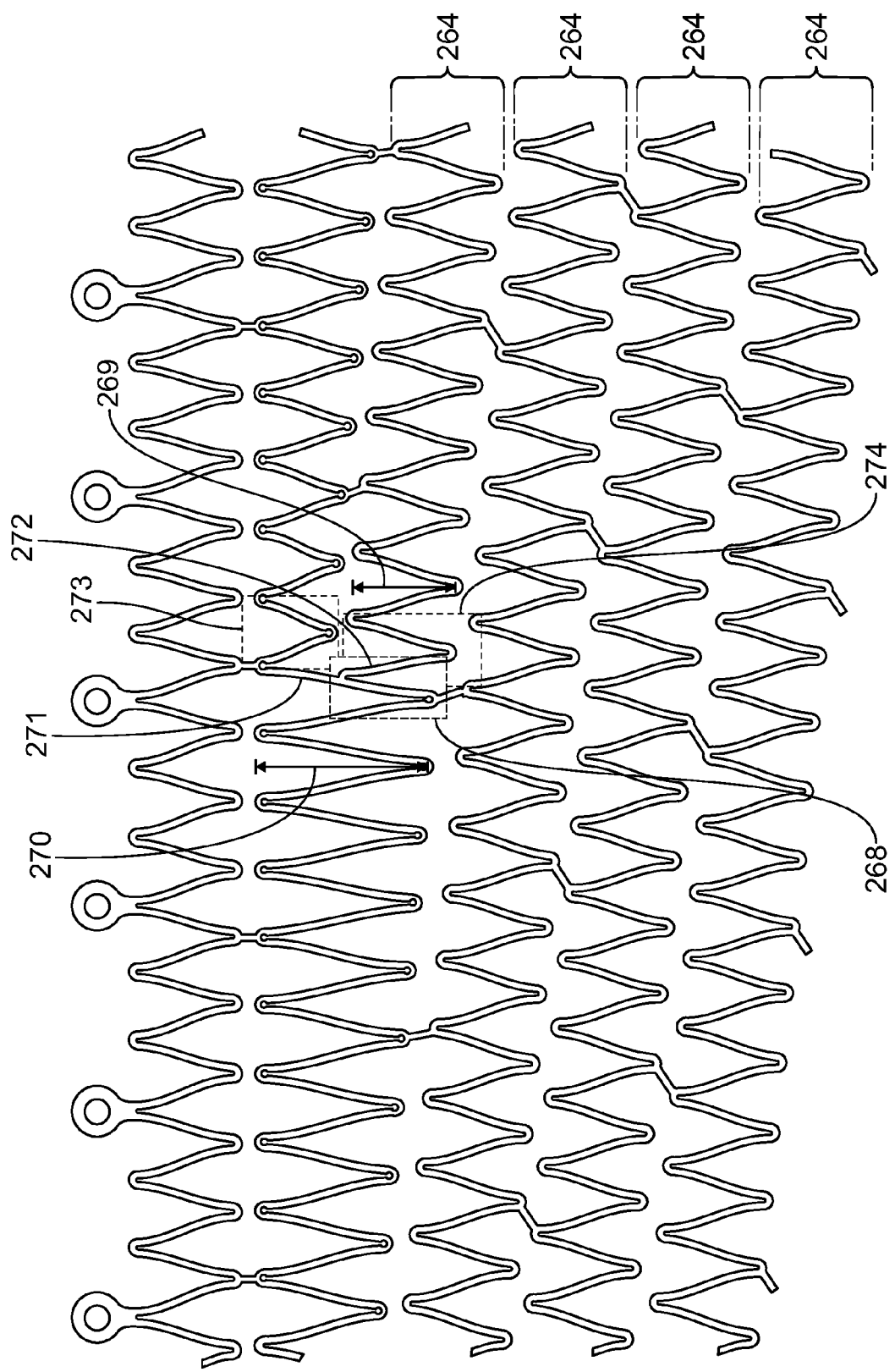
Figure 25A:
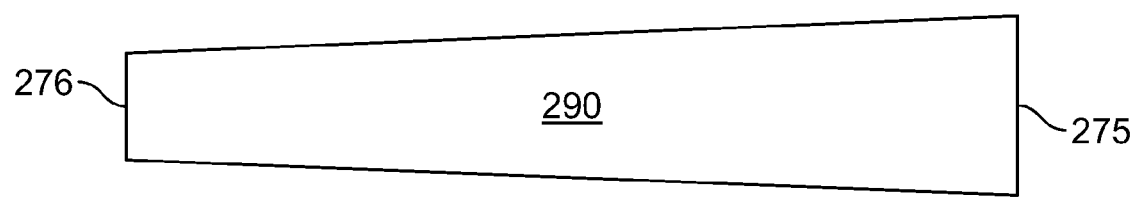
Figure 25B:
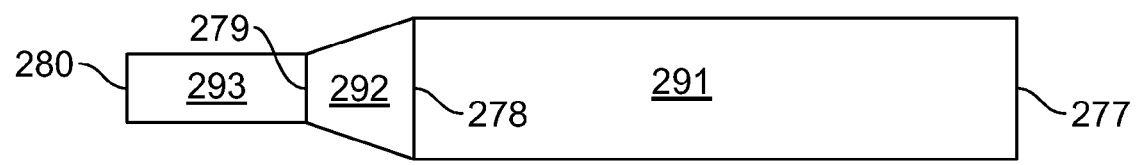
Figure 25C:
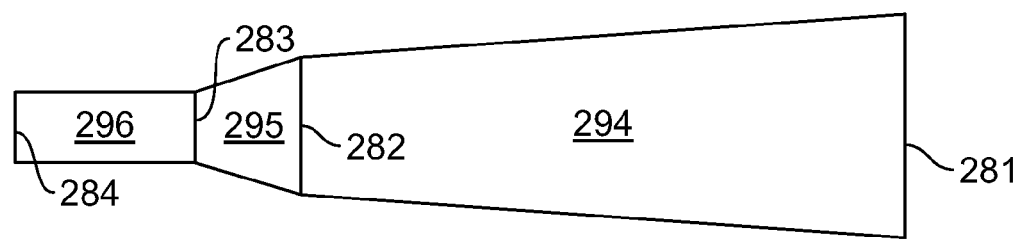
Figure 25D:
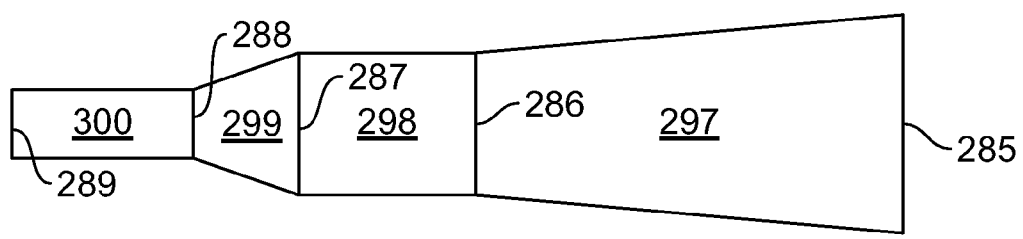

The junction zone 268 between the main body 164 and the transition zone 165 can assume a variety of different configurations. In the embodiment shown in FIG. 24, the amplitude 266 of the second undulations of the cylindrical windings 264 is less than the amplitude 270 of the undulations of the transition zone 165; specifically, compare 269 and 270 At the juncture zone 268, segment 272 of the undulation of the cylindrical windings 264 intersects a segment 271 of the transition zone 165 at a point approximately ⅓ along its length. Note, segment 271 connects two undulations, 273, 274. In another embodiment, the amplitude of the undulations in the main body 164 is equal to the amplitude of the undulations in the transition zone 165.

A variety of different segment designs are encompassed in the transition zone including zone such as those found in U.S. Pat. Nos. 6,696,402 and 6,878,162 are encompassed by the present invention. For example, the junction can comprise a the trident which is comprised of two struts of a common hoop at the end of the transition zone, as well as an adjacent strut which is connected to either the beginning of the transition zone or the helical portion. The junction of the trident includes the hinge of the common hoop, as well as a hinge connecting the adjacent strut to the hinge of the common hoop. U.S. Pat. No. 6,969,402.

The main body 164 of the stent can assume a variety of different configurations. As shown in FIGS. 25a to 25d the main body of the stent can taper. For example, the diameter of one end of the stent 275 may be greater than the diameter of the other end of the stent 276 forming a tapered main body 290. The main body 164 may be formed from three sections 291, 292 and 293 where the ends of the sections 291 have equal diameters 277=278, section 292 comprises a tapered section where diameters 278 is greater than 279. Section 293 is uptapered with diameters 279=280. In another embodiment, section 294, diameter 281 is greater than 282, section 295, 282 is greater than 283, and in section 296, diameters 283=284. Another embodiment shows two tapered sections 297 and 299 where diameters 285, 287 are greater than 286 and 288, respectively. Sections where no tapering is present 298 and 300 have constant diameters at either end, 286=287 and 288=289.

The device of the present invention may be used with any suitable catheter, the diameter of which may range from about 0.8 mm to about 5.5 mm, from about 1.0 mm to about 4.5 mm, from about 1.2 mm to about 2.2 mm, or from about 1.8 to about 3 mm. In one embodiment, the catheter is about 6 French (2 mm) in diameter. In another embodiment, the catheter is about 5 French (1.7 mm) diameter. The device of the present invention may be used as a self-expanding stent or with any balloon catheter stent delivery system, including balloon catheter stent delivery systems described in U.S. Pat. Nos. 6,168,617, 6,222,097, 6,331,186 and 6,478,814. In one embodiment, the present device is used with the balloon catheter system disclosed in U.S. Pat. No. 7,169,162. The subjects that can be treated using the stent and methods of this invention are mammals, including a human, horse, dog, cat, pig, rodent, monkey and the like.

The methods of treatment of vascular disease illustrated herein can be practiced on any artery or vein. Included within the scope of this invention is atherosclerosis of any artery such as coronary, infrainguinal, aortoiliac, subclavian, mesenteric and renal arteries. Other types of vessel obstructions, such as those resulting from a dissecting aneurysm are also encompassed by the invention.

The stent of the present invention may be formed from metal such as nickel-titanium (Ni—Ti). A metal composition and process of manufacturing the device is disclosed in U.S. Pat. No. 6,013,854. The super elastic metal for the device is preferably a super elastic alloy. A super elastic alloy is generally called "a shape-memory alloy" and resumes its original shape after being deformed to such a degree that an ordinary metal undergoes permanent deformation. Super elastic alloys useful in the invention include: Elgiloy® and Phynox® spring alloys (Elgiloy® alloy is available from Carpenter Technology Corporation of Reading Pa.; Phynox® alloy is available from Metal Imphy of Imphy, France), 316 stainless steel and MP35N alloy which are available from Carpenter Technology corporation and Latrobe Steel Company of Latrobe, Pa., and superelastic Nitinol nickel-titanium alloy which is available from Shape Memory Applications of Santa Clara, Calif. U.S. Pat. No. 5,891,191.

Alternatively, the device may be composed of self-expanding, bioabsorbable polymeric compositions, such as those disclosed in applicant's co pending provisional Patent Application No. US 61/104,718, filed on Oct. 11, 2008, entitled "Bioabsorbable Polymeric Compositions and Medical Devices". Pharmaceutical compositions may be incorporated into the polymers or may be coated on the surface of the polymers after mixing and extrusion by spraying, dipping or painting or microencapsulated and then blended into the polymer mixture. U.S. Pat. No. 6,020,385. If the pharmaceutical compositions are covalently bound to the polymer blend, they may be linked by hetero- or homo-bifunctional cross linking agents (see, http://www.piercenet.com/products/browse.cfm?fldID=020306).

Pharmaceutical compositions that may be incorporated into the polymers or may be coated on the polymers and can include (i) pharmacological agents such as, (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, thymidine kinase inhibitors, rapamycin, 40-0-(2-Hydroxyethyl)rapamycin (everolimus), 40-0-Benzyl-rapamycin, 40-0(4'-Hydroxymethyl)benzyl-rapamycin, 40-0-[4'-(1,2-Dihydroxyethyl)]benzyl-rapamycin, 40-Allyl-rapamycin, 40-0-[3'-(2,2-Dimethyl-1,3-dioxolan-4(S)-yl-prop-2'-en-1'-yl]-20 rapamycin, (2':E,4'S)-40-0-(4',5'-: Dihydroxypent-2'-en-1'-yl), rapamycin 40-0(2Hydroxy) ethoxycar-bonylmethyl-rapamycin, 40-0-(3-Hydroxypropyl-rapamycin 40-0-((Hydroxy)hexyl-rapamycin 40-0-[2-(2-Hydroxy)ethoxy]ethyl-rapamycin, 40-0-[(3S)-2,2Dimethyldioxolan-3-yl]methyl-rapamycin, 40-0-[(2S)-2,3-Dihydroxyprop-1-yl]-rapamycin, 40-0-(2-Acctoxy)ethyl-rapamycin, 40-0-(2-Nicotinoyloxy)ethyl-rapamycin, 40-0-[2-(N-25 Morpholino) acetoxyethyl-rapamycin, 40-0-(2-N-Imidazolylacetoxy)ethyl-rapamycin, 40-0[2-(N-Methyl-N'-piperazinyl)acetoxy]ethyl-rapamycin, 39-0-Desmethyl-3.9, 40-0,0 ethylene-rapamycin, (26R)-26-Dihydro-40-0-(2-hydroxy)ethyl-rapamycin, 28-O Methyrapamycin, 40-0-(2-Aminoethyl)-rapamycin, 40-0-(2-Acetaminoethyl)-rapamycin 40-0(2-Nicotinamidoethyl)-rapamycin, 40-0-(2-(N-Methyl-imidazo-2' ylcarbcthoxamido)ethyl)-30 rapamycin, 40-0-(2-Ethoxycarbonylaminoethyl)-rapamycin, 40-0-(2-Tolylsulfonamidoethyl)-rapamycin, 40-0-[2-(4',5'-Dicarboethoxy-1',2';3'-triazol-1'-yl)-ethyl]rapamycin, 42-Epi-(telrazolyl)rapamycin (tacrolimus), and 42-[3-hydroxy-2-(hydroxymethyl)-2-methylpropanoate]rapamycin (temsirolimus) (WO2008/086369); (d) anesthetic agents such as lidocaine, bupivacaine and ropivacaine; (e) anticoagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and, (o) agents that interfere with endogenous vasoactive mechanisms, (ii) genetic therapeutic agents include anti-sense DNA and RNA as well as DNA coding for (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor a and P, platelet-derived endothelial growth factor, platelet-derived growth factor, tumor necrosis factor a, hepatocyte growth factor and insulin-like growth factor, (d) cell cycle inhibitors including CD inhibitors, and (e) thymidine kinase ("TK") and other agents useful for interfering with cell proliferation.

Other pharmaceutical agents that may be incorporated into the polymer blends, include, acarbosc, antigens, beta-receptor blockers, non-steroidal antiinflammatory drugs (NSAID;, cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomcthasone, betahistine, bezafibrate, bicalutamide, diazepam and diazepam derivatives, budesonide, bufexamac, buprcnorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidinc, cotrimoxazole, codeine, caffeine, vitamin D and derivatives of vitamin D, colestyramine, cromoglicic acid, coumarin and coumarin derivatives, cysteine, cytarabine, cyclophosphamide, cyclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, erythropoietin and erythropoietin derivatives, morphinans, calcium antagonists, irinotecan, modafmil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, ctofibrate, fcno flbrate, etofylHne, etoposide, famciclovir, famotidine, felodipine, fenoftbrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mcpindolol, meprobamate, meropenem, mesalazinc, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastinc, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tctracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazolinc, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobutcrol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorclbinc, vinpocetine, viquidil, warfarin, xantinol nicotinate, xipamide, zafirlukast, zalcitabine, zidovudine, zolmitriptan, Zolpidem, zoplicone, zotipine and the like. See, e.g., U.S. Pat. Nos. 6,897,205, 6,838,528 and 6,497,729.

The stent may also be coated with antibodies or polymeric matrices which are capable of capturing circulating endothelial cells. U.S. Pat. No. 7,037,772 (see also, U.S. Patent Publications Nos. 20070213801, 200701196422, 20070191932, 20070156232, 20070141107, 20070055367, 20070042017, 20060135476, 20060121012).

The stent of the present invention may also be formed from bioabsorbable polymers represent a wide range of different polymers. Typically, bioabsorbable polymers comprise aliphatic polyesters based on lactide backbone such as poly L-lactide, poly D-lactide, poly D,L-lactide, mesolactide, glycolides, lactones, as homopolymers or copolymers, as well as formed in copolymer moieties with co-monomers such as, trimethylene carbonate (TMC) or ε-caprolactone (ECL). U.S. Pat. Nos. 6,706,854 and 6,607,548; EP 0401844; and Jeon et al. *Synthesis and Characterization of Poly (L-lactide)—Poly (ε-caprolactone)*. Multiblock Copolymers Macromolecules 2003: 36, 5585-5592. The copolymers comprises a moiety such as L-lactide or D-lactide of sufficient length that the copolymer can crystallize and not be sterically hindered by the presence of glycolide, polyethylene glycol (PEG), ε-caprolactone, trimethylene carbonate or monomethoxy-terminated PEG (PEG-MME). For example, in certain embodiments greater than 10, 100 or 250 L or D-lactides may be arrayed sequentially in a polymer.

The device may be made, for example, by forming a pipe of a super elastic material and then removing the parts of the pipe where the notches or holes are to be formed. As a result, the device comprises a single piece without having any abrupt change in the physical property of the stent as would result from welding. The notches and holes can be formed in the pipe by laser (YAG laser, for example), electrical discharge, chemical etching, mechanical cutting, or a combined use of any of these techniques. U.S. Pat. No. 5,879,381. The device of the present invention may be manufactured in numerous ways. The device may be formed from a tube by removing various portions of the tube's wall to form the patterns described herein. The resulting device will thus be formed from a single contiguous piece of material, eliminating the need for connecting various segments together. Material from the tube wall may be removed using various techniques including laser (YAG laser for example), electrical discharge, chemical etching, metal cutting, a combination of these techniques, or other well known techniques. U.S. Pat. Nos. 5,879,381 and 6,117,165. Forming stents in this manner allows for creation of a substantially stress-free structure where the helical segments are integral with the circumferential elements. In one embodiment, the tube from which the device is formed may have an internal diameter of about 3.0 mm, a wall thickness of about 1.0 mm and a length of about 30 mm. Tubes having other dimensions may be used. In particular, the length may be adapted to that of the diseased part of the lumen in which the stent is to be placed. This may avoid using separate stents to cover the total diseased area.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

We claim:

1. A stent comprising:
    a main body formed from a plurality of first cylindrical windings wherein adjacent cylindrical windings are connected by at least one first strut, further comprising,
    a transition zone disposed at one end of the main body, the transition zone comprising a plurality of polygons, wherein surface area of the polygons across the transition zone increases circumferentially relative to the long axis of the stent,
    each polygon of the plurality of polygons comprises a first undulation comprising a plurality of segments and a second undulation comprising a plurality of segments, and two connecting segments directly connecting a segment from the plurality of segments of the first undulation and a segment of the plurality of segments of the second undulation to connect the first undulation and the second undulation,
    the length of each of the segments of the plurality of segments in the first and second undulations are equal within each polygon, and
    the connecting segments connecting the first and second undulations increase in length circumferentially relative to the long axis of the stent
    wherein the bending moment of the first undulation and the second undulation in each polygon is equal, and the bending moment of the first and second undulations remains constant across the transition zone.

2. The stent of claim 1 wherein adjacent polygons have unequal surface areas.

3. The stent of claim 2 where the surface area of the polygons increases in a clockwise manner relative to the long axis of the stent.

4. The stent of claim 2 where the surface area of the polygons increases in a counterclockwise manner relative to the long axis of the stent.

5. The stent of claim 1 wherein the two segments connecting the first undulation and the second undulation in each polygon are substantially parallel to each other in a crimped configuration relative to the long axis of the stent.

6. The stent of claim 1 further comprising an end zone disposed at either end of the main body, wherein the end zone is attached to the transition zone by at least one third strut.

7. The stent of claim 6 wherein the end zone comprises at least one second cylindrical winding.

8. The stent of claim 7 further comprising at least one radiopaque marker.

9. The stent of claim 1 wherein the plurality of first cylindrical windings propagate helically.

10. The stent of claim 1 wherein each polygon of the plurality of polygons is a hexagon.

11. The stent of claim 10 wherein the length of each segments in the first and second undulations are equal across the transition zone.

12. The stent of claim 1 wherein the plurality of first cylindrical windings comprise a plurality of third undulations and wherein each third undulation comprises two segments.

13. The stent of claim 12 wherein the two segments are linear.

14. The stent of claim 12 wherein the two segments are curvilinear.

15. The stent of claim 12 wherein the number of segments between two first struts is 3, 5, 6, 7, 8, 9 or 10.

16. The stent of claim 1 further comprising an end zone disposed at either end of the main body, wherein the end zone is attached to the transition zone by at least one third strut.

17. The stent of claim 16 wherein the end zone comprises at least one second cylindrical winding.

18. The stent of claim 17 further comprising a radiopaque marker.

19. The stent of claim 1 wherein the segments are linear.

20. The stent of claim 1 wherein the segments are curvilinear.

* * * * *